(12) United States Patent
Wong et al.

(10) Patent No.: US 9,073,941 B2
(45) Date of Patent: Jul. 7, 2015

(54) COMPOUNDS AND METHODS FOR TREATING TUBERCULOSIS INFECTION

(75) Inventors: Chi-Huey Wong, Rancho Santa Fe, CA (US); Ying-Ta Wu, Taipei (TW)

(73) Assignee: Academia Sinica, Taipei (TW)

(*) Notice: Subject to any disclaimer, the term of this patent is extended or adjusted under 35 U.S.C. 154(b) by 238 days.

(21) Appl. No.: 13/806,228

(22) PCT Filed: Jun. 28, 2011

(86) PCT No.: PCT/US2011/042217
§ 371 (c)(1),
(2), (4) Date: Mar. 7, 2013

(87) PCT Pub. No.: WO2012/006104
PCT Pub. Date: Jan. 12, 2012

(65) Prior Publication Data
US 2013/0158037 A1 Jun. 20, 2013
US 2013/0345223 A9 Dec. 26, 2013

Related U.S. Application Data

(60) Provisional application No. 61/358,992, filed on Jun. 28, 2010.

(51) Int. Cl.
| | |
|---|---|
| A61K 31/415 | (2006.01) |
| C07D 498/04 | (2006.01) |
| C07C 49/753 | (2006.01) |
| C07C 49/755 | (2006.01) |
| C07D 401/12 | (2006.01) |
| C07D 405/14 | (2006.01) |
| C07D 413/14 | (2006.01) |
| C07D 417/14 | (2006.01) |
| C07D 487/04 | (2006.01) |

(52) U.S. Cl.
CPC ............ *C07D 498/04* (2013.01); *C07C 49/753* (2013.01); *C07C 49/755* (2013.01); *C07D 401/12* (2013.01); *C07D 405/14* (2013.01); *C07D 413/14* (2013.01); *C07D 417/14* (2013.01); *C07D 487/04* (2013.01)

(58) Field of Classification Search
None
See application file for complete search history.

(56) References Cited

U.S. PATENT DOCUMENTS

| | | |
|---|---|---|
| 4,061,836 A | 12/1977 | Yundt |
| 5,514,505 A | 5/1996 | Limburg et al. |
| 5,563,014 A | 10/1996 | Malhotra et al. |
| 5,709,737 A | 1/1998 | Malhotra et al. |
| 2002/0035251 A1 | 3/2002 | Zhang et al. |
| 2007/0135439 A1 | 6/2007 | Guedat et al. |

FOREIGN PATENT DOCUMENTS

| | | |
|---|---|---|
| KR | 2010/0113204 A | 10/2010 |
| RU | 2263667 C1 * | 11/2005 |
| WO | WO 01/79209 A2 | 10/2001 |
| WO | WO 02/26707 A1 | 4/2002 |
| WO | WO 03/001968 A2 | 1/2003 |
| WO | WO 2004/007498 A2 | 1/2004 |
| WO | WO 2005/007141 A2 | 1/2005 |
| WO | WO 2006/116764 A1 | 11/2006 |
| WO | WO 2007144394 A2 * | 12/2007 |
| WO | WO 2008/039876 A1 | 4/2008 |
| WO | WO 2009/088990 A1 | 7/2009 |
| WO | WO 2010/003533 A2 | 1/2010 |
| WO | WO 2010/014798 A2 | 2/2010 |
| WO | WO 2010/072807 A2 | 7/2010 |
| WO | WO 2010/079238 A1 | 7/2010 |
| WO | WO 2010/131921 A2 | 11/2010 |
| WO | WO 2010/135608 A1 | 11/2010 |
| WO | WO 2011/000481 A1 | 1/2011 |
| WO | WO 2011/043254 A1 | 4/2011 |

OTHER PUBLICATIONS

STN Print of RU2263667, Mar. 12, 2015.*
[No Author Listed] Centers for Disease Control and Prevention (CDC). Emergence of *Mycobacterium tuberculosis* with extensive resistance to second-line drugs—worldwide, 2000-2004. MMWR Morb Mortal Wkly Rep. Mar. 24, 2006;55(11):301-5.
Brubaker et al., Synthesis and rat lens aldose reductase inhibitory activity of some benzopyran-2-ones. J Med Chem. Jun. 1986;29(6):1094-9.
Bryk et al., Metabolic enzymes of mycobacteria linked to antioxidant defense by a thioredoxin-like protein. Science. Feb. 8, 2002;295(5557):1073-7. Epub Jan. 17, 2002.
Geetanjali et al., Synthesis of 2-Aroyl-3-phenylfuranobenzopyrones. Indian Journal of Chemistry. 1983;22B:164-165.
Limaye, Chem. Ber. 1934;67:12-14. German.
Rajashankar et al., Crystal structure and functional analysis of lipoamide dehydrogenase from *Mycobacterium tuberculosis*. J Biol Chem. Oct. 7, 2005;280(40):33977-83. Epub Aug. 10, 2005.

* cited by examiner

*Primary Examiner* — Jeffrey S Lundgren
*Assistant Examiner* — Michael Schmitt
(74) *Attorney, Agent, or Firm* — Wolf, Greenfield & Sacks, P.C.

(57) ABSTRACT

The present invention provides compounds which are potent inhibitors against Lpd activity, PDH activity, and/or the growth of *tubercle bacillus*, and thus are useful in the treatment of tuberculosis infection and associated conditions. The present invention is further directed to in vitro- and in vzivo-based methods of inhibiting Lpd and/or PDH activity. In certain embodiments, these methods are useful in inhibiting Lpd and/or PDH activity key to a pathogen's survival.

20 Claims, 4 Drawing Sheets

COMPOUNDS AND METHODS FOR TREATING TUBERCULOSIS INFECTION

RELATED APPLICATIONS

This application is a national stage filing under 35 U.S.C. §371 of international PCT application PCT/US2011/042217, filed Jun. 28, 2011, which claims the benefit under 35 U.S.C. §119(e) of U.S. provisional application, U.S. Ser. No. 61/358,992, filed Jun. 28, 2010, each of which is herein incorporated by reference in its entirety.

BACKGROUND OF THE INVENTION

Tuberculosis (TB, *tubercle bacillus*) is a common and in many cases lethal infectious disease caused by various strains of mycobacteria, usually *Mycobacterium tuberculosis* (Mtb). Typical symptoms include cough accompanied by blood, fever, night sweats, and weight loss. Tuberculosis usually attacks the lungs ("pulmonary tuberculosis") but can also affect other parts of the body. Infection of other organs, collectively denoted extrapulmonary tuberculosis, causes a wide range of symptoms. Extrapulmonary infection sites include the pleura in tuberculous pleurisy, the central nervous system in meningitis, the lymphatic system in scrofula of the neck, the genitourinary system in urogenital tuberculosis, and bones and joints in Pott's disease of the spine. An especially serious form of extrapulmonary tuberculosis is disseminated tuberculosis, more commonly known as miliary tuberculosis. Extrapulmonary tuberculosis may co-exist with pulmonary tuberculosis.

Diagnosis of tuberculosis relies on radiology, tuberculin skin tests, blood tests, as well as microscopic examination and microbiological culture of bodily fluids. Treatment is difficult and requires long courses of multiple antibiotics. As a result, antibiotic resistance to this antibiotic regimen is a growing problem. In recent years the incidence of tuberculosis, especially multidrug-resistant tuberculosis (MDR-TB) and extensively-drug-resistant tuberculosis (XDR-TB), has increased alarmingly. The World Health Organization (WHO) reports an estimated 6.6 million cases of tuberculosis in 1990, to 8.3 million cases of tuberculosis in 2000, to 9.27 million tuberculosis cases in 2007.

Various enzymes of *tubercle bacillus* are involved in the defense of oxidative and nitrosative stress in macrophage, such as lipoamide dehydrogenase (Lpd), dihydrolipoamide acyltransferase (DlaT; formerly termed succinyl transferase), alkylhydroperoxidase (AhpC), and the protein (AhpD) encoded by an adjacent gene. See, e.g., Bryk et al., *Science* (2002) 295:1073-1077 and Rajashankar et al., *Journal of Biological Chemistry* (2005) 280:33977-33983. All of these enzymes contain redox centers that reduce or oxidize adjacent partners in the pathway and have been attractive targets for therapeutic intervention against tuberculosis. Other infections which may be treated via inhibition of Lpd include, but are not limited to, *Pseudomonas aeruginosa* and *Trypanosoma brucei* infection. Both Lpd and DlaT are components of the multienzyme form pyruvate dehydrogenase (PDH) complex. Lpd belongs to group I flavoprotein disulfide reductase protein family and constitutes the E3 component of PDH. Lpd catalyzes the NAD-dependent oxidation of the dihydrolipoyl cofactor that is covalently linked to the lipoyl domain of DlaT, the E2 component of PDH.

It is clear there continues to remain a need for new therapeutics for the treatment of pathogenic diseases such as tuberculosis and associated conditions. Such therapeutics may target key pathways in a pathogen's survival, such as inhibiting lipoamide dehydrogenase (Lpd) and/or pyruvate dehydrogenase (PDH) activity.

SUMMARY OF THE INVENTION

This invention is based on the discovery that certain compounds disclosed herein are potent inhibitors against Lpd activity, PDH activity, and/or the growth of *tubercle bacillus*, e.g., *Mycobacterium tuberculosis*, and thus are useful in the treatment of tuberculosis infection and associated conditions. The present invention is further directed to in vitro- and in vivo-based methods of inhibiting Lpd and/or PDH activity. In certain embodiments, these methods are useful in inhibiting Lpd and/or PDH activity key to a pathogen's survival.

This application refers to various issued patent, published patent applications, journal articles, and other publications, all of which are incorporated herein by reference.

The details of one or more embodiments of the invention are set forth herein. Other features, objects, and advantages of the invention will be apparent from the Description, the Figures, the Examples, and the Claims.

DEFINITIONS

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "alkyl" refers to an straight or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is unsubstituted $C_{1-20}$ alkyl (e.g., —$CH_3$). In certain embodiments, the alkyl group is substituted $C_{1-20}$ alkyl.

The term "alkylene" refers to a divalent alkyl group, i.e., an alkyl group as defined herein which is connected to the parent molecule via the removal of two or more hydrogen atoms.

The term "alkenyl" refers to a straight or branched hydrocarbon group containing one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), 1,4-butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is unsubstituted $C_{2-20}$ alkenyl. In certain embodiments, the alkenyl group is substituted $C_{2-20}$ alkenyl.

The term "alkynyl" refers to a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is unsubstituted $C_{2-20}$ alkynyl. In certain embodiments, the alkynyl group is substituted $C_{2-20}$ alkynyl.

The term "cycloalkyl" refers to a saturated monocyclic, bicyclic, or tricyclic hydrocarbon ring system having 3 to 10 carbon atoms ("$C_{3-10}$ cycloalkyl") and zero heteroatoms in the ring system. "Cycloalkyl" also includes ring systems wherein the cycloalkyl ring is fused with one or more aryl or heteroaryl groups wherein the point of attachment is on the cycloalkyl ring, and in such instances, the number of carbons continue to designate the number of carbons in the cycloalkyl ring system. In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Exemplary $C_{3-6}$ cycloalkyl groups include, without limitation, cyclopropyl ($C_3$), cyclobutyl ($C_4$), cyclopentyl ($C_5$), cyclohexyl ($C_6$), and the like. Exemplary $C_{3-8}$ cycloalkyl groups include, without limitation, the aforementioned $C_{3-6}$ cycloalkyl groups as well as cycloheptyl ($C_7$), cyclooctyl ($C_8$), bicyclo[2.2.1]heptanyl ($C_7$), bicyclo[2.2.2]octanyl ($C_8$), and the like. Exemplary $C_{3-10}$ cycloalkyl groups include, without limitation, the aforementioned $C_{3-8}$ cycloalkyl groups as well as cyclononyl ($C_9$), cyclodecyl ($C_{10}$) octahydro-1H-indenyl ($C_9$), decahydronaphthalenyl ($C_{10}$), spiro[4.5]decanyl ($C_{10}$), adamantanyl ($C_{10}$), and the like. Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

The term "cycloalkenyl" refers to non-aromatic monocyclic, bicyclic, or tricyclic hydrocarbon ring system having 3 to 10 carbon atoms ("$C_{3-10}$ cycloalkyl"), one or more double bonds, and zero heteroatoms in the ring system. "Cycloalkenyl" also includes ring systems wherein the cycloalkenyl ring is fused with one or more aryl or heteroaryl groups wherein the point of attachment is on the cycloalkenyl ring, and in such instances, the number of carbons continue to designate the number of carbons in the cycloalkenyl ring system. In some embodiments, a cycloalkenyl group has 3 to 8 ring carbon atoms ("$C_{3-8}$ cycloalkenyl"). In some embodiments, a cycloalkenyl group has 3 to 6 ring carbon atoms ("$C_{3-6}$ cycloalkenyl"). In some embodiments, a cycloalkenyl group has 5 to 6 ring carbon atoms ("$C_{5-6}$ cycloalkenyl"). In some embodiments, a cycloalkyl group has 5 to 10 ring carbon atoms ("$C_{5-10}$ cycloalkenyl"). Exemplary $C_{3-6}$ cycloalkenyl groups include, without limitation, cyclopropenyl ($C_3$), cyclobutenyl ($C_4$), cyclopentenyl ($C_5$), cyclohexenyl ($C_6$), cyclohexadienyl ($C_6$), and the like. Exemplary $C_{3-8}$ cycloalkenyl groups include, without limitation, the aforementioned $C_{3-6}$ cycloalkenyl groups as well as cycloheptenyl ($C_7$), cycloheptadienyl ($C_7$), cycloheptatrienyl ($C_7$), cyclooctenyl ($C_8$), and the like. Exemplary $C_{3-10}$ cycloalkenyl groups include, without limitation, the aforementioned $C_{3-8}$ cycloalkenyl groups as well as cyclononenyl ($C_9$), cyclodecenyl ($C_{10}$), and the like. Unless otherwise specified, each instance of a cycloalkenyl group is independently unsubstituted (an "unsubstituted cycloalkenyl") or substituted (a "substituted cycloalkenyl") with one or more substituents. In certain embodiments, the cycloalkenyl group is unsubstituted $C_{3-10}$ cycloalkenyl. In certain embodiments, the cycloalkenyl group is substituted $C_{3-10}$ cycloalkenyl.

The term "heterocycloalkyl" refers to a saturated 5-8 membered monocyclic, 8-12 membered bicyclic, or 11-14 membered tricyclic ring system (collectively referred to as a "3-14 membered heterocycloalkyl") having ring carbon atoms and one to four heteroatoms ring heteroatoms, wherein each heteroatom is independently selected from the group consisting of oxygen, nitrogen, sulfur, phosphorus, boron, silicon, and selenium. In heterocycloalkyl groups that contain one or more nitrogen atoms, the point of attachment can be a carbon or nitrogen atom, as valency permits. A heterocycloalkyl group can either be monocyclic ("monocyclic heterocycloalkyl") or a fused, bridged or spiro ring system such as a bicyclic system ("bicyclic heterocycloalkyl"). Heterocycloalkyl bicyclic ring systems can include one or more heteroatoms in one or both rings. "Heterocycloalkyl" also includes ring systems wherein the heterocycloalkyl ring, as defined above, is fused with one or more cycloalkyl or cycloalkenyl groups wherein the point of attachment is either on either ring, or ring systems wherein the heterocycloalkyl ring, as defined above, is fused with one or more aryl or heteroaryl groups, wherein the point of attachment is on the heterocycloalkyl ring, and in such instances, the number of ring members continue to designate the number of ring members in the heterocycloalkyl ring system. Unless otherwise specified, each instance of heterocycloalkyl is independently unsubstituted (an "unsubstituted heterocycloalkyl") or substituted (a "substituted heterocycloalkyl") with one or more substituents. In certain embodiments, the heterocycloalkyl group is unsubstituted 5-10 membered heterocycloalkyl. In certain embodiments, the heterocycloalkyl group is substituted 5-10 membered heterocycloalkyl.

In some embodiments, a heterocycloalkyl group is a 5-10 membered ring system having ring carbon atoms and 1-4 ring heteroatoms ("5-10 membered heterocycloalkyl"). In some embodiments, a heterocycloalkyl group is a 5-8 membered ring system having ring carbon atoms and 1-4 ring heteroatoms ("5-8 membered heterocycloalkyl"). In some embodiments, a heterocycloalkyl group is a 5-6 membered ring system having ring carbon atoms and 1-4 ring heteroatoms ("5-6 membered heterocycloalkyl"). In some embodiments, the 5-6 membered heterocycloalkyl has 1-3 ring heteroatoms. In some embodiments, the 5-6 membered heterocycloalkyl has 1-2 ring heteroatoms. In some embodiments, the 5-6 membered heterocycloalkyl has one ring heteroatom.

Exemplary 5-membered heterocycloalkyl groups containing one heteroatom include, without limitation, tetrahydrofuranyl, dihydrofuranyl, tetrahydrothiophenyl, and pyrrolidinyl. Exemplary 5-membered heterocycloalkyl groups containing two heteroatoms include, without limitation, dioxolanyl, oxasulfuranyl, and disulfuranyl. Exemplary 5-membered heterocycloalkyl groups containing three heteroatoms include, without limitation, triazolinyl, oxadiazolinyl, and thiadiazolinyl. Exemplary 6-membered heterocycloalkyl groups containing one heteroatom include, without limitation, piperidinyl, tetrahydropyranyl, and thianyl. Exemplary 6-membered heterocycloalkyl groups containing two heteroatoms include, without limitation, piperazinyl, morpholinyl, dithianyl, and dioxanyl. Exemplary 7-membered heterocycloalkyl groups containing one heteroatom include, without limitation, azepanyl, oxepanyl, and thiepanyl. Exemplary 8-membered heterocycloalkyl groups containing one heteroatom include, without limitation, azocanyl, oxecanyl, and thiocanyl.

The term "heterocycloalkenyl" refers to a nonaromatic 5-8 membered monocyclic, 8-12 membered bicyclic, or 11-14 membered tricyclic ring system (collectively referred to as a "3-14 membered heterocycloalkenyl") having ring carbon atoms and one to four heteroatoms ring heteroatoms, wherein each heteroatom is independently selected from the group consisting of oxygen, nitrogen, sulfur, phosphorus, boron, silicon, and selenium. In heterocycloalkenyl groups that contain one or more nitrogen atoms, the point of attachment can be a carbon or nitrogen atom, as valency permits. A heterocycloalkenyl group can either be monocyclic ("monocyclic heterocycloalkenyl") or a fused, bridged or spiro ring system such as a bicyclic system ("bicyclic heterocycloalkenyl"). Heterocycloalkenyl bicyclic ring systems can include one or more heteroatoms in one or both rings. "Heterocycloalkenyl" also includes ring systems wherein the heterocycloalkenyl ring, as defined above, is fused with one or more cycloalkyl or cycloalkenyl groups wherein the point of attachment is either on either ring, or ring systems wherein the heterocycloalkenyl ring, as defined above, is fused with one or more aryl or heteroaryl groups, wherein the point of attachment is on the heterocycloalkenyl ring, and in such instances, the number of ring members continue to designate the number of ring members in the heterocycloalkenyl ring system. Unless otherwise specified, each instance of heterocycloalkenyl is independently unsubstituted (an "unsubstituted heterocycloalkenyl") or substituted (a "substituted heterocycloalkenyl") with one or more substituents. In certain embodiments, the heterocycloalkenyl group is unsubstituted 5-10 membered heterocycloalkenyl. In certain embodiments, the heterocycloalkenyl group is substituted 5-10 membered heterocycloalkenyl.

In some embodiments, a heterocycloalkenyl group is a 5-10 membered ring system having ring carbon atoms and 1-4 ring heteroatoms ("5-10 membered heterocycloalkenyl"). In some embodiments, a heterocycloalkenyl group is a 5-8 membered ring system having ring carbon atoms and 1-4 ring heteroatoms ("5-8 membered heterocycloalkenyl"). In some embodiments, a heterocycloalkenyl group is a 5-6 membered ring system having ring carbon atoms and 1-4 ring heteroatoms ("5-6 membered heterocycloalkenyl"). In some embodiments, the 5-6 membered heterocycloalkenyl has 1-3 ring heteroatoms. In some embodiments, the 5-6 membered heterocycloalkenyl has 1-2 ring heteroatoms. In some embodiments, the 5-6 membered heterocycloalkenyl has one ring heteroatom.

Exemplary 5-membered heterocycloalkenyl groups containing one heteroatom include, without limitation, dihydrothiophenyl, dihydropyrrolyl, 3,4-dihydropyrrol-2-one, and pyrrolyl-2,5-dione. Exemplary 6-membered heterocycloalkenyl groups containing one heteroatom include, without limitation, dihydropyridinyl. Exemplary bicyclic heterocycloalkenyl groups include, without limitation, indolinyl, isoindolinyl, dihydrobenzofuranyl, dihydrobenzothienyl, tetrahydroquinolinyl, tetrahydroisoquinolinyl, decahydroquinolinyl, and decahydroisoquinolinyl, and the like.

The term "aryl" refers to a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of "alkyl" and refers to an optionally substituted alkyl group, as defined herein, substituted by an optionally substituted aryl group, as defined herein, wherein the point of attachment is on the alkyl moiety.

"Arylalkenyl" is a subset of "alkenyl" and refers to an optionally substituted alkenyl group, as defined herein, substituted by an optionally substituted aryl group, as defined herein, wherein the point of attachment is on the alkenyl moiety.

The term "heteroaryl" refers to an aromatic 5-8 membered monocyclic or polycyclic (i.e., 8-12 membered bicyclic, or 11-14 membered tricyclic) ring system (collectively referred to as a "5-14 membered heteroaryl") having ring carbon atoms and one to four heteroatoms ring heteroatoms, wherein each heteroatom is independently selected from the group consisting of oxygen, nitrogen, sulfur, phosphorus, boron, silicon, and selenium. In heteroaryl groups that contain one or more nitrogen atoms, the point of attachment can be a carbon or nitrogen atom, as valency permits. Heteroaryl bicyclic or tricyclic ring systems can include one or more heteroatoms in one more of the rings. "Heteroaryl" includes ring systems wherein the heteroaryl ring, as defined above, is fused with one or more cycloalkyl, cycloalkenyl, heterocycloalkyl, or heterocycloalkenyl, wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system ("5-10 membered heteroaryl"). In some embodiments, a heteroaryl group is a 5-8 membered aromatic ring system having ring carbon atoms and 1-4 ring heteroatoms provided in the aromatic ring system ("5-8 membered heteroaryl"). In some embodiments, a heteroaryl group is a 5-6 membered aromatic ring system having ring carbon atoms and 1-4 ring heteroatoms provided in the aromatic ring system ("5-6 membered heteroaryl"). In some embodiments, the 5-6 membered heteroaryl has 1-3 ring heteroatoms. In some embodiments, the 5-6 membered heteroaryl has 1-2 ring heteroatoms. In some embodiments, the 5-6 membered heteroaryl has 1 ring heteroatom. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, purinyl, [1,2,3]triazolo[4,5-b]pyrazinyl, [1,2,5]thiadiazolo[3,4-b]pyrazinyl, and [1,2,5]oxadiazolo[3,4-b]pyrazinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of "alkyl" and refers to an optionally substituted alkyl group, as defined herein, substituted by an optionally substituted heteroaryl group, as defined herein, wherein the point of attachment is on the alkyl moiety.

"Heteroarylalkenyl" is a subset of "alkenyl" and refers to an optionally substituted alkenyl group, as defined herein, substituted by an optionally substituted heteroaryl group, as defined herein, wherein the point of attachment is on the alkenyl moiety.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl moieties) as herein defined. Likewise, "saturated" refers to a group that does not contain a double or triple bond, i.e., contains all single bonds.

Alkyl, alkenyl, alkynyl, cycloalkyl, cycloalkenyl, heteroalkyl, heteroalkenyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" cycloalkyl, "substituted" or "unsubstituted" cycloalkenyl, "substituted" or "unsubstituted" heteroalkyl, "substituted" or "unsubstituted" heteroalkenyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Alkyl, alkenyl, alkynyl, cycloalkyl, heterocycloalkyl, cycloalkenyl, heterocycloalkenyl, aryl, and heteroaryl mentioned above include both substituted and unsubstituted moieties. Exemplary substituents on cycloalkyl, heterocycloalkyl, cycloalkenyl, heterocycloalkenyl, aryl, and heteroaryl include, but are not limited to, alkyl, alkenyl, alkynyl, cycloalkyl, cycloalkenyl, heterocycloalkyl, heterocycloalkenyl, aryl, heteroaryl, alkoxy, aryloxy, heteroaryloxy, amino (—NH$_2$), alkylamino, arylamino, heteroarylamino, hydroxy (—OH), halo (—F, —Br, —I, —Cl), oxo (O=) thioxo (S=), thio (—SH), silyl, thioacyl, acylthio, alkylthio, arylthio, alkylsulfonyl, arylsulfonyl, heteroarylsulfonyl, aminoacyl, aminothioacyl, amidino, amido, thioureido, thiocyanato (—SCN), sulfonamide, guanidino, ureido, cyano (—CN), nitro (—NO$_2$), acyl, thioacyl, acyloxy, carbamido, carbamyl, carboxylic acid (—COOH), and carboxylic ester. Exemplary substituents on alkyl, alkenyl, or alkynyl include all of the above-recited substituents except alkyl, alkenyl, or alkynyl.

The term "alkoxy" or "alkyloxy" refers to an —O-alkyl radical, wherein alkyl is optionally substituted alkyl as defined herein. Examples of alkoxy include, but are not limited to, methoxy, ethoxy, n-propoxy, isopropoxy, n-butoxy, iso-butoxy, sec-butoxy, and tert-butoxy.

The term "aryloxy" refers to an —O-aryl, wherein aryl is optionally substituted aryl as defined herein.

The term "heteroaryloxy" refers to an —O-heteroaryl, wherein heteroaryl is optionally substituted heteroaryl as defined herein.

The term "acyl" refers to an —C(=O)R radical in which R is selected from the group consisting of hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl.

The term "acyloxy" refers to an —OC(=O)R radical in which R is selected from the group consisting of optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl.

The term "alkylthio" refers to an —S-alkyl radical, wherein alkyl is optionally substituted alkyl as defined herein. Examples of alkoxy include, but are not limited to, methoxy, ethoxy, n-propoxy, isopropoxy, n-butoxy, iso-butoxy, sec-butoxy, and tert-butoxy.

The term "arylthio" refers to an —S-aryl, wherein aryl is optionally substituted aryl as defined herein.

The term "heteroarylthio" refers to an —S-heteroaryl, wherein heteroaryl is optionally substituted heteroaryl as defined herein.

The term "acylthio" refers to an —SC(=O)R radical in which R is selected from the group consisting of optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl.

The term "thioacyl" refers to an —C(=O)SR radical in which R is selected from the group consisting of optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl.

The term "amino" refers to —NH$_2$, alkylamino, or arylamino.

The term "alkylamino" refers to the group —N(R)-alkyl, in which alkyl is optionally substituted alkyl, as defined herein, and each instance of R is independently selected from the group consisting of hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl.

The term "arylamino" refers to an —N(R)-aryl, in which aryl is optionally substituted aryl, as defined herein, and each instance of R is independently selected from the group consisting of hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl.

The term "heteroarylamino" refers to an —N(R)-heteroaryl, in which heteroaryl is optionally substituted heteroaryl, as defined herein, and each instance of R is independently selected from the group consisting of hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl.

The term "amido" or "amino acyl" refers to —NRC(=O)R' in which each of R and R', independently, is selected from the group consisting of hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl.

The term "aminothioacyl" refers to —NRC(=S)R' in which each instance of R and R', independently, is selected from the group consisting of hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl.

The term "amidino" refers to —NRC(=NR)R' or —C(=NR)NRR' in which each instance of R and R', independently, is selected from the group consisting of hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl.

The term "carbamido" or "acylamino" refers to —C(=O)NRR' in which each of R and R', independently, is selected from the group consisting of hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl. The term "carbamyl" is a subset of carbamido, and refers to the group —C(O)NH$_2$, i.e., wherein R and R' are both hydrogen.

The term "ureido" refers to —NRC(=O)NRR' in which each of R and R', independently, is selected from the group consisting of hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl.

The term "thioureido" refers to —NRC(=S)NRR' in which each of R and R', independently, is selected from the group consisting of hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl.

The term "guanidino" refers to —NRC(=NR)NRR' in which each of R and R', independently, is selected from the group consisting of hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl.

The term "silyl" refers to a group —SiR$_3$ in which each of R independently is selected from the group consisting of optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl The term "alkylsulfonyl" refers to the group —SO$_2$-alkyl, wherein alkyl is optionally substituted alkyl as defined herein.

The term "arylsulfonyl" refers to the group —SO$_2$-aryl, wherein aryl is optionally substituted aryl as defined herein.

The term "heteroarylsulfonyl" refers to the group —SO$_2$-heteroaryl, wherein heteroaryl is optionally substituted heteroaryl as defined herein.

The term "sulfonamide" or "sulfonamido" refers to the group —SO$_2$NRR', —SO$_2$NHR', —SO$_2$NH$_2$, —NHSO$_2$R', or —NRSO$_2$R' in which each of R and R', independently, is selected from the group consisting of optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl.

The term "carboxylic ester" refers to —CO$_2$R in which R is selected from the group consisting of optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, and optionally substituted heteroaryl.

Nitrogen and oxygen protecting groups (also respectively referred to as amino and hydroxyl protecting groups) are known in the art and include those described in detail in *Protecting Groups in Organic Synthesis*, T. W. Greene and P. G. M. Wuts, 3$^{rd}$ edition, John Wiley & Sons, 1999, incorporated herein by reference.

Nitrogen atoms may be protected in a variety of ways, for example, as amides, carbamates, sulfonamides, and the like. Exemplary amide nitrogen protecting groups include but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide. Exemplary carbamate nitrogen protecting groups include, but are not limited to, methyl carbamate, ethyl carbamante, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate. Exemplary sulfonamide nitrogen protecting groups include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8' dimethoxynaphthylmethyl)benzenesulfonamide (DNMBS), benzylsulfonamide, trifluoromethylsulfonamide, and phenacylsulfonamide. Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

These and other exemplary substituents are described in more detail in the Detailed Description, Examples, and claims. The invention is not intended to be limited in any manner by the above exemplary listing of substituents.

Other Definitions

"Salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, quaternary salts.

"Tautomer" includes two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

The term "hydrate" refers to a compound of the present disclosure non-covalently associated with one or more molecules of water. Likewise, a "solvate" refers to a compound of the present disclosure non-covalently associated with one or more molecules of an organic solvent.

The term "prodrug" refers to a compound which, upon administration to a subject, is metabolized in vivo to the parent compound. An examples of a prodrug is an ester which is hydrolyzed to the carboxylic acid.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

As used herein, "inhibiting," "inhibition," "inhibit," "inhibitor," and the like, refer to the ability of a compound to reduce, slow, halt, or prevent activity of a particular biological process (e.g., Lpd or PDH activity) in a cell relative to vehicle.

The term "treating," "treatment," or "treat" refers to the administration of a compound of the present invention to a subject in need thereof with the purpose to confer a therapeutic effect, e.g., to cure, relieve, alter, affect, ameliorate, or prevent a tuberculosis infection, a symptom associated with such an infection, or a predisposition toward it (e.g., prevent relapsed tuberculosis infection). In certain embodiments, the subject suffers from tuberculosis (e.g., an Mtb infection), or exhibits one or more symptoms associated with tuberculosis. Such a subject can be diagnosed by a health care professional based on results from any suitable diagnostic method.

"An effective amount" refers to the amount of one or more compounds of the present invention that is required to confer a therapeutic or prophylactic effect on a treated subject. Effective amounts may vary, as recognized by those skilled in the art, depending on route of administration, excipient usage, and the possibility of co-usage with other agents.

A "therapeutically effective amount" of a compound is an amount sufficient to provide a therapeutic benefit in the treatment of an infection or to delay or minimize one or more symptoms associated with the infection.

A "prophylactically effective amount" of a compound is an amount sufficient to prevent the infection or prevent its recurrence.

DETAILED DESCRIPTION OF CERTAIN EMBODIMENTS OF THE INVENTION

Figure 1:
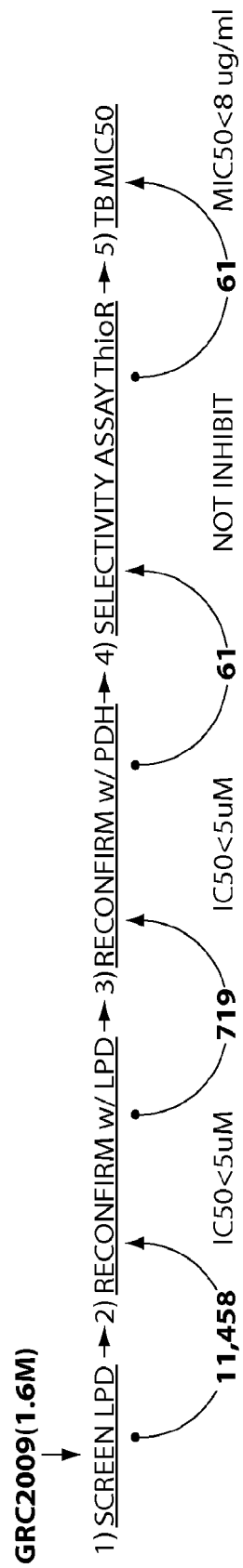
FIG. 1 depicts the high throughput screening (HTS) procedure.
Figure 2:
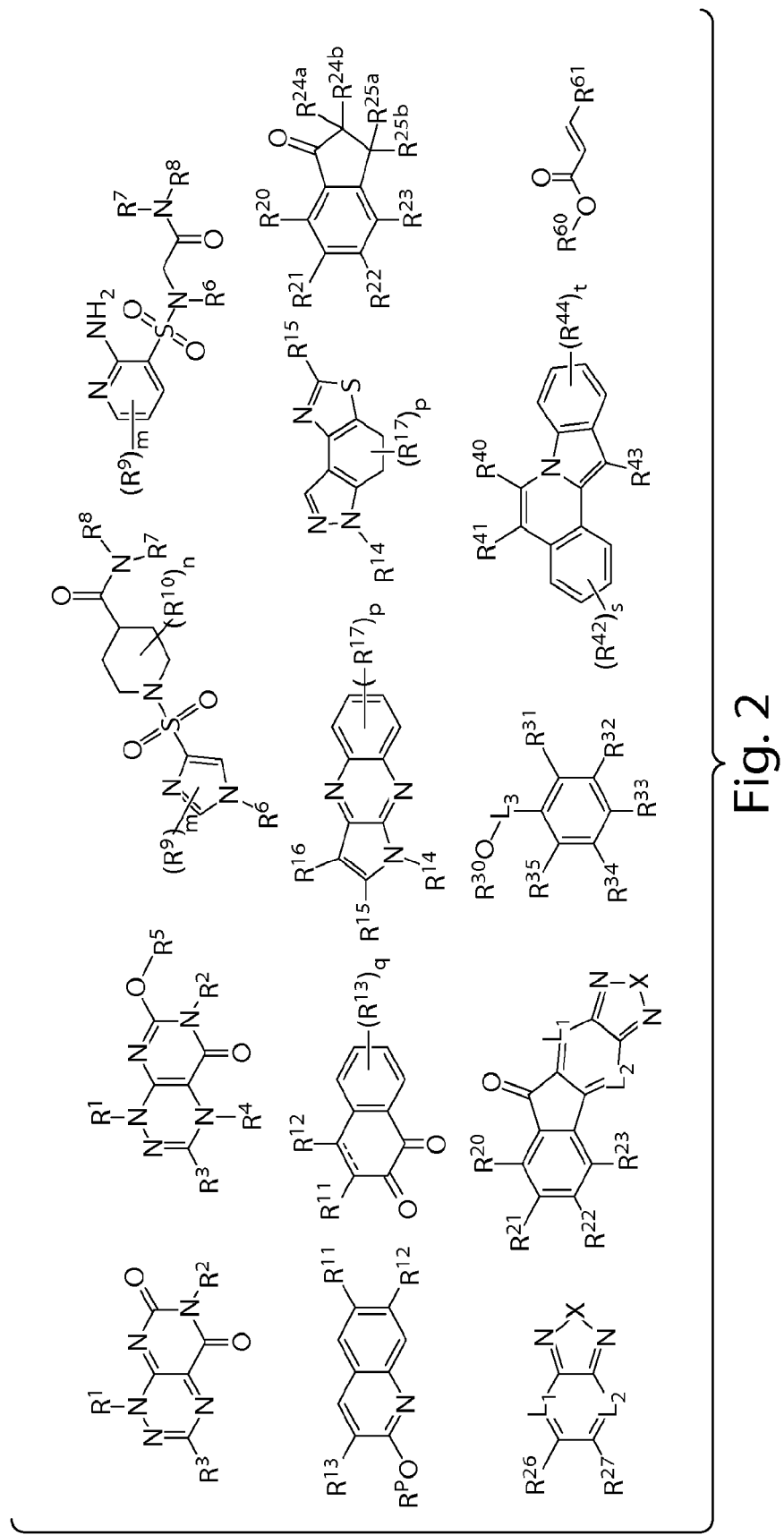
FIG. 2 depicts various structural classes screened.
Figure 3A:
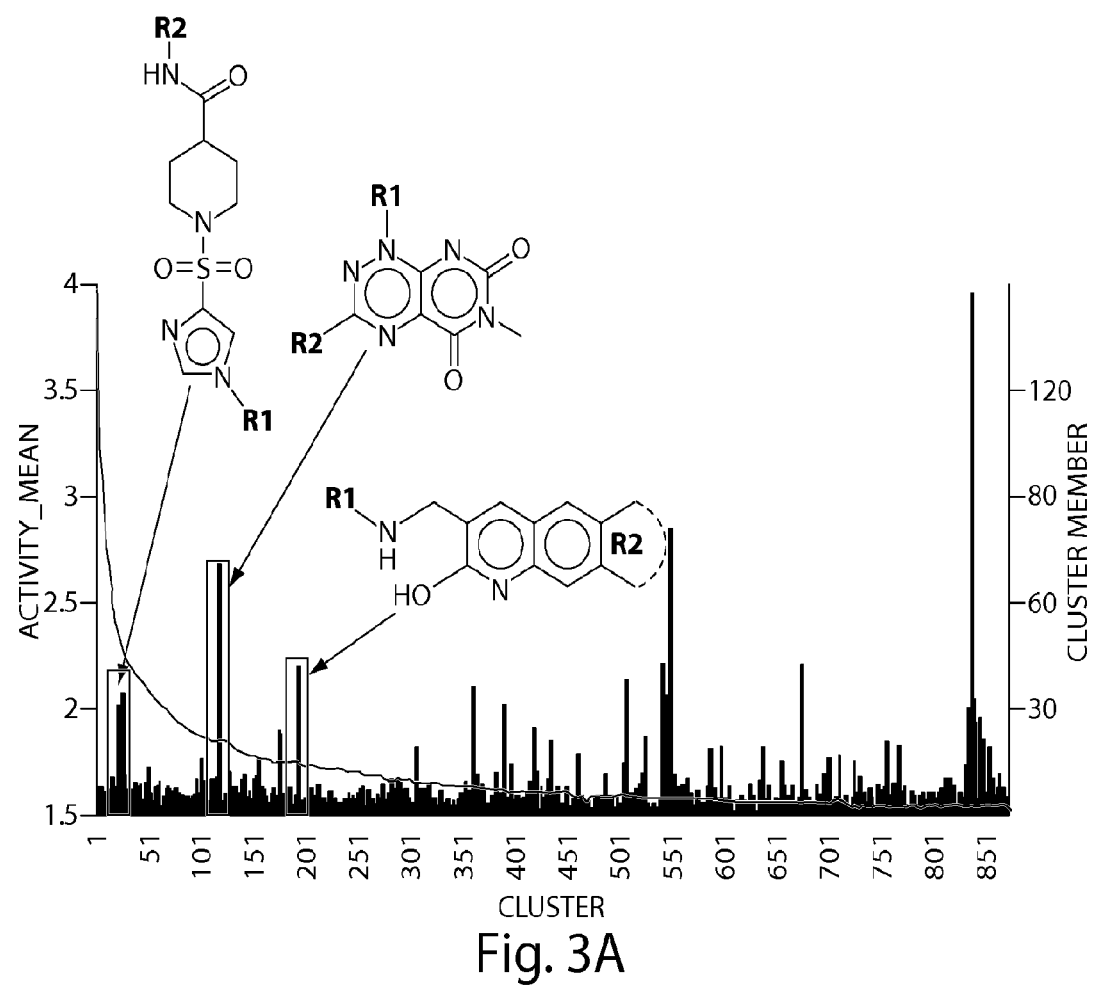
FIG. 3 depicts the most frequent scaffolds (FIG. 3A) and specific members of these scaffolds showing high inhibitory activity (FIG. 3B).
Figure 3B:
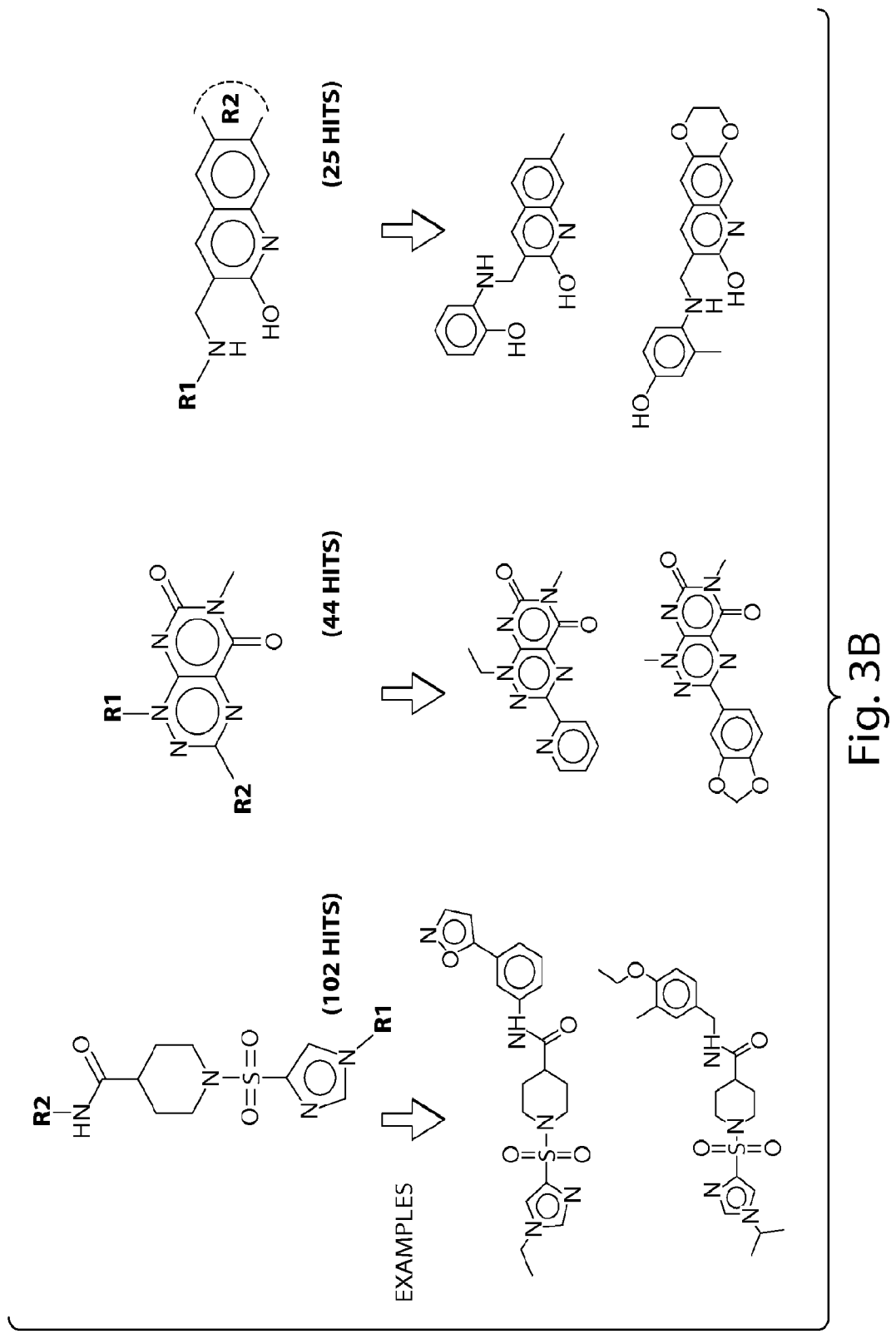

It has been found that compounds encompassed by one or more of Formulae:

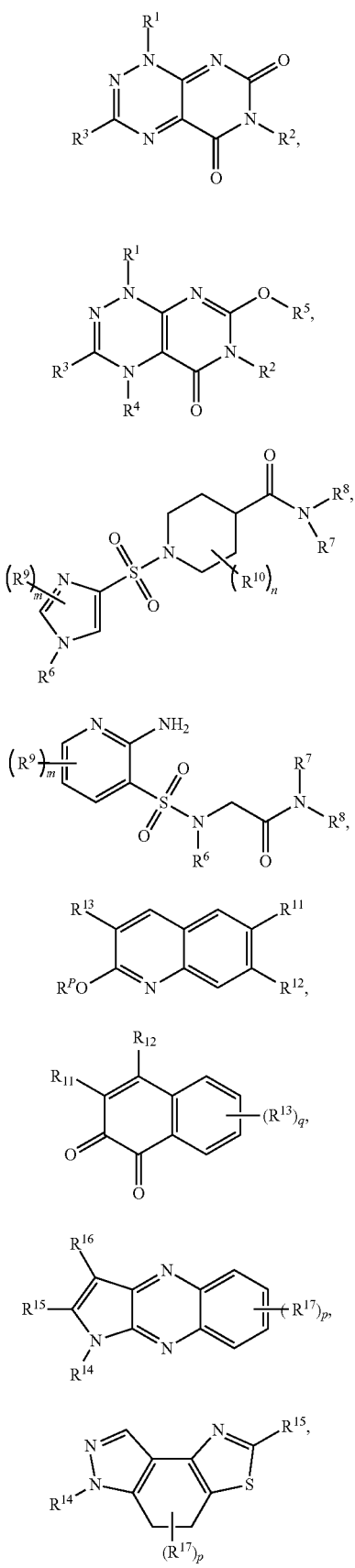

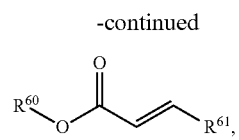

(XVI)

are potent inhibitors against lipoamide dehydrogenase (Lpd) activity, pyruvate dehydrogenase (PDH) activity, and/or the growth of *tubercle bacillus*, e.g., *Mycobacterium tuberculosis*, and thus are useful in the treatment of tuberculosis infection (e.g., pulmonary tuberculosis, extrapulmonary tuberculosis, and/or disseminated tuberculosis infection) and associated conditions, such as tuberculous pleurisy, meningitis, scrofula of the neck, urogenital tuberculosis, and Pott's disease of the spine. In certain embodiments, the compounds of the present invention are useful in the treatment of a *Mycobacterium tuberculosis* (Mtb) infection.

The present invention also provides methods for inhibiting lipoamide dehydrogenase (Lpd) activity comprising contacting a lipoamide dehydrogenase with an effective amount of a compound of the present invention. The present invention further provides methods for inhibiting pyruvate dehydrogenase activity comprising contacting a pyruvate dehydrogenase (PDH) with an effective amount of a compound of the present invention. Such methods encompasses in vitro (assay) methods as well as in vivo (treatment) methods. In certain embodiments, these methods are useful in inhibiting Lpd and/or PDH activity key to a pathogen's survival.

Compounds of Formula (I)

In one aspect, the present invention provides a compound of Formula (I), e.g., for example, a compound for use in the treatment of a tuberculosis infection:

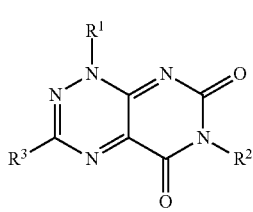

(I)

or a pharmaceutically acceptable salt thereof, or a tautomer thereof;
wherein:
each instance of $R^1$ and $R^2$, independently, is hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, or an amino protecting group;

$R^3$ is hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, CN, $OR_a$, $COOR_a$, $OC(O)R_a$, $C(O)R_a$, $C(O)NR_bR_c$, or $NR_bR_c$;

each instance of $R_a$ is independently hydrogen, optionally substituted alkyl, optionally substituted cycloalkyl, optionally substituted cycloalkenyl, optionally substituted heterocycloalkyl, optionally substituted heterocycloalkenyl, optionally substituted aryl, or optionally substituted heteroaryl; and each instance of $R_b$ and $R_c$ is, independently, hydrogen, optionally substituted alkyl, optionally substituted cycloalkyl, optionally substituted cycloalkenyl, optionally substituted heterocycloalkyl, optionally substituted heterocycloalkenyl, optionally substituted aryl, optionally substituted heteroaryl, an amino protecting group, or $R_b$ and $R_c$, together with the nitrogen atom to which they are bonded are an optionally substituted heterocycloalkyl, an optionally substituted heterocycloalkenyl, or an optionally substituted heteroaryl.

In certain embodiments of Formula (I), $R^1$ is hydrogen. In certain embodiments of Formula (I), $R^1$ is optionally substituted alkyl, e.g., optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. In certain embodiments of Formula (I), $R^1$ is an unsubstituted alkyl group, e.g., in certain embodiments, $R^1$ is $—CH_3$ or $—CH_2CH_3$. In certain embodiments of Formula (I), $R^1$ is an amino protecting group as defined herein.

In certain embodiments of Formula (I), $R^2$ is hydrogen. In certain embodiments of Formula (I), $R^2$ is optionally substituted alkyl, e.g., optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. In certain embodiments of Formula (I), $R^2$ is an unsubstituted alkyl group, e.g., in certain embodiments, $R^2$ is $—CH_3$ or $—CH_2CH_3$. In certain embodiments of Formula (I), $R^2$ is an amino protecting group as defined herein.

In certain embodiments, each instance of $R^1$ and $R^2$ of Formula (I) is independently, optionally substituted alkyl. For example, in certain embodiments of Formula (I), each instance of $R^1$ and $R^2$ is independently $—CH_3$ or $—CH_2CH_3$.

In certain embodiments of Formula (I), $R^3$ is optionally substituted aryl, optionally substituted heteroaryl, optionally substituted aralkyl, optionally substituted heteroarylalkyl, optionally substituted arylalkenyl, or optionally substituted heteroarylalkenyl.

In certain embodiments of Formula (I), $R^3$ is optionally substituted alkyl, e.g., optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. In certain embodiments of Formula (I), $R^3$ is an unsubstituted alkyl group, e.g., in certain embodiments, $R^3$ is $—CH_3$, $—CH_2CH_3$, or $—CH_2CH_2CH_3$. However, in certain embodiments of Formula (I), $R^3$ is a substituted alkyl group, e.g., in certain embodiments, $R^3$ is optionally substituted aralkyl, e.g., optionally substituted aryl-$C_1$alkyl (e.g., optionally substituted benzyl) or optionally substituted aryl-$C_2$alkyl. In certain embodiments, $R^3$ is optionally substituted heteroarylalkyl, e.g., optionally substituted heteroaryl-$C_1$alkyl or optionally substituted heteroaryl-$C_2$alkyl.

In certain embodiments of Formula (I), $R^3$ is optionally substituted alkenyl, e.g., optionally substituted $C_2$ alkenyl, optionally substituted $C_3$ alkenyl, optionally substituted $C_4$ alkenyl, optionally substituted $C_5$ alkenyl, or optionally substituted $C_6$ alkenyl. In certain embodiments of Formula (I), $R^3$ is an unsubstituted alkenyl group, e.g., in certain embodiments, $R^3$ is $—CH_2CH=CH_2$. However, in certain embodiments of Formula (I), $R^3$ is a substituted alkenyl group, e.g., in certain embodiments, $R^3$ is optionally substituted arylalkenyl, e.g., optionally substituted aryl-$C_2$alkenyl (e.g., $C_6H_5$—

C$_2$alkenyl). In certain embodiments, R$^3$ is optionally substituted heteroarylalkenyl, e.g., optionally substituted heteroaryl-C$_2$alkenyl.

In certain embodiments of Formula (I), R$^3$ is optionally substituted aryl, e.g., a monosubstituted phenyl, a disubstituted phenyl, or the phenyl ring is fused to a heterocylic ring, e.g., such as a 1,3-dioxolanyl ring. In certain embodiments of Formula (I), R$^3$ is a monosubstituted phenyl, e.g., substituted at the ortho, meta, or para position relative to the point of attachment. In certain embodiments of Formula (I), R$^3$ is a disubstituted phenyl, e.g., substituted at the 1,2-, 1,3-, 1,4-, 1,5-, 2,3-, or 2,4-position relative to the point of attachment. In certain embodiments, the phenyl ring is substituted with at least one substituent (e.g., 1, 2, 3, or 4 substituents) selected from the group consisting of halogen (e.g., —F, —Br, —I, —Cl), alkoxy, C$_{1-4}$alkyl, —NO$_2$, —CF$_3$, and a carboxylic ester. However, in certain embodiments of Formula (I), the phenyl ring is unsubstituted.

In certain embodiments of Formula (I), R$^3$ is optionally substituted heteroaryl, e.g., optionally substituted 5-membered heteroaryl or optionally substituted 6-membered heteroaryl. In certain embodiments of Formula (I), R$^3$ is optionally substituted 5-membered heteroaryl, e.g., optionally substituted thiophenyl, optionally substituted furanyl, or optionally substituted pyrrolyl. In certain embodiments of Formula (I), R$^3$ is optionally substituted 6-membered heteroaryl, e.g., optionally substituted pyridinyl. In certain embodiments, the hetoaryl ring is substituted. However, in certain embodiments of Formula (I), the hetoaryl ring is unsubstituted.

In certain embodiments, the compound of Formula (I) is selected from any one of the compounds, or pharmaceutically acceptable salts thereof or tautomers thereof, depicted in Table 6 of the Examples.

Compounds of Formula (II)

In another aspect, the present invention provides a compound of Formula (II), e.g., for example, a compound for use in the treatment of a tuberculosis infection:

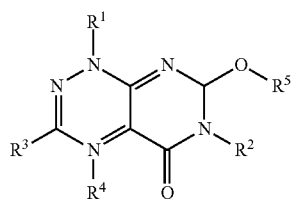

(II)

or pharmaceutically acceptable salt thereof, or tautomer thereof;
wherein:
each instance of R$^1$, R$^2$, and R$^4$, independently, is hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, or an amino protecting group;
R$^3$ is hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, CN, OR$_a$, COOR$_a$, OC(O)R$_a$, C(O)R$_a$, C(O)NR$_b$R$_c$, or NR$_b$R$_c$;
R$^5$ is hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted eterocycloalkenyl, optionally substituted aryl, optionally substituted heteroaryl, or a hydroxyl protecting group;
each instance of R$_a$ is independently hydrogen, optionally substituted alkyl, optionally substituted cycloalkyl, optionally substituted cycloalkenyl, optionally substituted heterocycloalkyl, optionally substituted heterocycloalkenyl, optionally substituted aryl, or optionally substituted heteroaryl; and
each instance of R$_b$ and R$_c$ is, independently, hydrogen, optionally substituted alkyl, optionally substituted cycloalkyl, optionally substituted cycloalkenyl, optionally substituted heterocycloalkyl, optionally substituted heterocycloalkenyl, optionally substituted aryl, optionally substituted heteroaryl, an amino protecting group, or R$_b$ and R$_c$, together with the nitrogen atom to which they are bonded are an optionally substituted heterocycloalkyl, an optionally substituted heterocycloalkenyl, or an optionally substituted heteroaryl.

In certain embodiments of Formula (II), R$^1$ is hydrogen. In certain embodiments of Formula (II), R$^1$ is optionally substituted alkyl, e.g., optionally substituted C$_1$alkyl, optionally substituted C$_2$alkyl, optionally substituted C$_3$alkyl, optionally substituted C$_4$alkyl, optionally substituted C$_5$alkyl, or optionally substituted C$_6$alkyl. In certain embodiments of Formula (II), R$^1$ is an unsubstituted alkyl group, e.g., in certain embodiments, R$^1$ is —CH$_3$ or —CH$_2$CH$_3$. In certain embodiments of Formula (II), R$^1$ is an amino protecting group as defined herein.

In certain embodiments of Formula (II), R$^2$ is hydrogen. In certain embodiments of Formula (II), R$^2$ is optionally substituted alkyl, e.g., optionally substituted C$_1$alkyl, optionally substituted C$_2$alkyl, optionally substituted C$_3$alkyl, optionally substituted C$_4$alkyl, optionally substituted C$_5$alkyl, or optionally substituted C$_6$alkyl. In certain embodiments of Formula (II), R$^2$ is an unsubstituted alkyl group, e.g., in certain embodiments, R$^2$ is —CH$_3$ or —CH$_2$CH$_3$. In certain embodiments of Formula (I), R$^2$ is an amino protecting group as defined herein.

In certain embodiments, each instance of R$^1$ and R$^2$ of Formula (II) is independently, optionally substituted alkyl. For example, in certain embodiments of Formula (II), each instance of R$^1$ and R$^2$ is independently —CH$_3$ or —CH$_2$CH$_3$.

In certain embodiments of Formula (II), R$^3$ is optionally substituted aryl, optionally substituted heteroaryl, optionally substituted aralkyl, optionally substituted heteroarylalkyl, optionally substituted arylalkenyl, or optionally substituted heteroarylalkenyl.

In certain embodiments of Formula (II), R$^3$ is optionally substituted alkyl, e.g., optionally substituted C$_1$alkyl, optionally substituted C$_2$alkyl, optionally substituted C$_3$alkyl, optionally substituted C$_4$alkyl, optionally substituted C$_5$alkyl, or optionally substituted C$_6$alkyl. In certain embodiments of Formula (II), R$^3$ is an unsubstituted alkyl group, e.g., in certain embodiments, R$^3$ is —CH$_3$, —CH$_2$CH$_3$, or —CH$_2$CH$_2$CH$_3$. However, in certain embodiments of Formula (II), R$^3$ is a substituted alkyl group, e.g., in certain embodiments, R$^3$ is optionally substituted aralkyl, e.g., optionally substituted aryl-C$_1$alkyl (e.g., optionally substituted benzyl) or optionally substituted aryl-C$_2$alkyl. In certain embodiments of Formula (II), R$^3$ is optionally substituted heteroarylalkyl, e.g., optionally substituted heteroaryl-$C_1$alkyl or optionally substituted heteroaryl-$C_2$alkyl.

In certain embodiments of Formula (II), $R^3$ is optionally substituted alkenyl, e.g., optionally substituted $C_2$ alkenyl, optionally substituted $C_3$ alkenyl, optionally substituted $C_4$ alkenyl, optionally substituted $C_5$ alkenyl, or optionally substituted $C_6$ alkenyl. In certain embodiments of Formula (I), $R^3$ is an unsubstituted alkenyl group, e.g., in certain embodiments, $R^3$ is —$CH_2CH=CH_2$. However, in certain embodiments of Formula (II), $R^3$ is a substituted alkenyl group, e.g., in certain embodiments of Formula (II), $R^3$ is optionally substituted arylalkenyl, e.g., optionally substituted aryl-$C_2$alkenyl (e.g., $C_6H_5$—$C_2$alkenyl). In certain embodiments of Formula (II), $R^3$ is optionally substituted heteroarylalkenyl, e.g., optionally substituted heteroaryl-$C_2$alkenyl.

In certain embodiments of Formula (II), $R^3$ is optionally substituted aryl, e.g., a monosubstituted phenyl, a disubstituted phenyl, or the phenyl ring is fused to a heterocylic ring, e.g., such as a 1,3-dioxolanyl ring. In certain embodiments of Formula (II), $R^3$ is a monosubstituted phenyl, e.g., substituted at the ortho, meta, or para position relative to the point of attachment. In certain embodiments of Formula (II), $R^3$ is a disubstituted phenyl, e.g., substituted at the 1,2-, 1,3-, 1,4-, 1,5-, 2,3-, or 2,4-position relative to the point of attachment. In certain embodiments of Formula (II), the phenyl ring is substituted with at least one substituent (e.g., 1, 2, 3, or 4 substituents) selected from the group consisting of halogen (e.g., —F, —Br, —I, —Cl), alkoxy, $C_{1-4}$ alkyl, —$NO_2$, —$CF_3$, and a carboxylic ester. However, in certain embodiments of Formula (II), the phenyl ring is unsubstituted.

In certain embodiments of Formula (II), $R^3$ is optionally substituted heteroaryl, e.g., optionally substituted 5-membered heteroaryl or optionally substituted 6-membered heteroaryl. In certain embodiments of Formula (II), $R^3$ is optionally substituted 5-membered heteroaryl, e.g., optionally substituted thiophenyl, optionally substituted furanyl, or optionally substituted pyrrolyl. In certain embodiments of Formula (II), $R^3$ is optionally substituted 6-membered heteroaryl, e.g., optionally substituted pyridinyl. In certain embodiments of Formula (II), the hetoaryl ring is substituted. However, in certain embodiments of Formula (II), the hetoaryl ring is unsubstituted.

In certain embodiments of Formula (II), each instance of $R^4$ and $R^5$ is independently hydrogen or optionally substituted alkyl.

In certain embodiments of Formula (II), $R^4$ is hydrogen. In certain embodiments of Formula (II), $R^4$ is optionally substituted alkyl, e.g., optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. In certain embodiments of Formula (II), $R^4$ is an unsubstituted alkyl group, e.g., in certain embodiments, $R^4$ is —$CH_3$, —$CH_2CH_3$, or —$CH_2CH_2CH_3$.

In certain embodiments of Formula (II), $R^5$ is hydrogen. In certain embodiments of Formula (II), $R^5$ is optionally substituted alkyl, e.g., optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. In certain embodiments of Formula (II), $R^5$ is an unsubstituted alkyl group, e.g., in certain embodiments, $R^5$ is —$CH_3$, —$CH_2CH_3$, or —$CH_2CH_2CH_3$.

In certain embodiments of Formula (II), each instance of $R^4$ and $R^5$ is independently hydrogen. In certain embodiments of Formula (II), each instance of $R^4$ and $R^5$ is independently optionally substituted alkyl.

In certain embodiments, the compound of Formula (II) is:

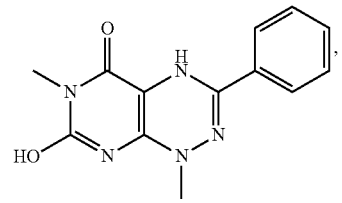 [SMILES: CN1N=C(c2ccccc2)Nc2c1nc(O)n(C)c2=O]

or a pharmaceutically acceptable salt or tautomer thereof.

Compound of Formula (V)

In another aspect, the present invention provides a compound of Formula (V), e.g., for example, a compound for use in the treatment of a tuberculosis infection:

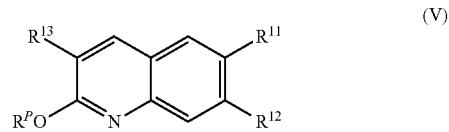

or a pharmaceutically acceptable salt thereof or tautomer thereof;
wherein:
each instance of $R^{11}$, $R^{12}$, and $R^{13}$, independently, is hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, —CN, —$OR_a$, —$COOR_a$, —OC(O)$R_a$, —C(O)$R_a$, —C(O)$NR_bR_c$, or —$NR_bR_c$;
$R^P$ is hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, or an oxygen protecting group;
each instance of $R_a$ is independently hydrogen, optionally substituted alkyl, optionally substituted cycloalkyl, optionally substituted cycloalkenyl, optionally substituted heterocycloalkyl, optionally substituted heterocycloalkenyl, optionally substituted aryl, or optionally substituted heteroaryl; and
each instance of $R_b$ and $R_c$ is, independently, hydrogen, optionally substituted alkyl, optionally substituted cycloalkyl, optionally substituted cycloalkenyl, optionally substituted heterocycloalkyl, optionally substituted heterocycloalkenyl, optionally substituted aryl, optionally substituted heteroaryl, an amino protecting group, or $R_b$ and $R_c$, together with the nitrogen atom to which they are bonded are an optionally substituted heterocycloalkyl, an optionally substituted heterocycloalkenyl, or an optionally substituted heteroaryl.

In certain embodiments of Formula (V), $R^P$ is hydrogen. In certain embodiments of Formula (V), $R^P$ is an oxygen protecting group.

In certain embodiments of Formula (V), $R^{11}$ is hydrogen, optionally substituted alkyl, —$NR_bR_c$, or —$OR_a$. In certain embodiments Formula (V), $R^{11}$ is hydrogen. In certain embodiments, $R^{11}$ is —$OR_a$, e.g., —$OCH_3$ or —$OCH_2CH_3$. In certain embodiments Formula (V), $R^{11}$ is optionally substituted alkyl, e.g., optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. In certain embodiments of Formula (V), $R^{11}$ is an unsubstituted alkyl group, e.g., in certain embodiments, $R^{11}$ is —$CH_3$ or —$CH_2CH_3$.

In certain embodiments of Formula (V), $R^{12}$ is hydrogen, optionally substituted alkyl, —$NR_bR_c$, or —$OR_a$. In certain embodiments Formula (V), $R^{12}$ is hydrogen. In certain embodiments, $R^{12}$ is —$OR_a$, e.g., —$OCH_3$ or —$OCH_2CH_3$. In certain embodiments Formula (V), $R^{12}$ is optionally substituted alkyl, e.g., optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. In certain embodiments of Formula (V), $R^{12}$ is an unsubstituted alkyl group, e.g., in certain embodiments, $R^{12}$ is —$CH_3$ or —$CH_2CH_3$.

In certain embodiments of Formula (V), $R^{11}$ and $R^{12}$, together with the carbon atoms to which they are bonded form an optionally substituted heterocycloalkyl, optionally substituted heterocycloalkenyl, optionally substituted aryl, or optionally substituted heteroaryl ring. In certain embodiments of Formula (V), $R^{11}$ and $R^{12}$, together with the carbon atoms to which they are bonded form an optionally substituted heterocycloalkyl, e.g., a 1,3-dioxanyl ring.

In certain embodiments of Formula (V), $R^{13}$ is hydrogen. In certain embodiments of Formula (V), $R^{13}$ is optionally substituted alkyl, e.g., alkyl optionally substituted with $NR_dR_e$, wherein each instance of $R_d$ and $R_e$, independently, is hydrogen, optionally substituted aryl, or optionally substituted heteroaryl. In certain embodiments of Formula (V), $R^{13}$ is —$CH_2NHR_e$, wherein $R_e$ is optionally substituted aryl or optionally substituted heteroaryl.

In certain embodiments of Formula (V), $R_e$ is optionally substituted aryl, e.g., a monosubstituted phenyl. In certain embodiments of Formula (V), $R_e$ is a monosubstituted phenyl, e.g., substituted at the ortho, meta, or para position relative to the point of attachment. In certain embodiments, the phenyl ring is monosubstituted, wherein the substituent is selected from the group consisting of —OH, alkoxy, —$NH_2$, or alkylamino. In certain embodiments, the phenyl ring is monosubstituted at the para position relative to the point of attachment.

In certain embodiments of Formula (V), $R_e$ is optionally substituted heteroaryl, e.g., optionally substituted 5,6- or 6,6-bicyclic heteroaryl. In certain embodiments, $R_e$ is an optionally substituted 5,6-heteroaryl, e.g., an optionally substituted indazolyl. In certain embodiments, the hetoaryl ring is substituted. However, in certain embodiments, the hetoaryl ring is unsubstituted.

In certain embodiments, the compound of Formula (V) is selected from any one of the compounds, or pharmaceutically acceptable salts or tautomers thereof, depicted in Table 8 of the Examples.

Compounds of Formula (VI)

In another aspect, the present invention provides a compound of Formula (VI), e.g., for example, a compound for use in the treatment of a tuberculosis infection:

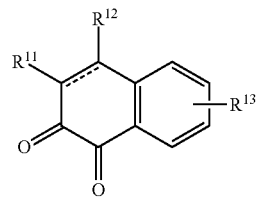

(VI)

or a pharmaceutically acceptable salt thereof, or tautomer thereof;

wherein:

----- represents a single or double bond;

each instance of $R^{11}$ and $R^{12}$, independently, is hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, —CN, —$OR_a$, —$COOR_a$, —OC(O)$R_a$, —C(O)$R_a$, —C(O)$NR_bR_c$, =$NR_b$, or —$NR_bR_c$, provided that ----- represents a single bond when $R^{11}$ or $R^{12}$ is =$NR_b$; or $R^{11}$ and $R^{12}$, together with the carbon atoms to which they are bonded form an optionally substituted cycloalkyl, optionally substituted cycloalkenyl, optionally substituted heterocycloalkyl, optionally substituted heterocycloalkenyl, optionally substituted aryl, or optionally substituted heteroaryl ring;

each instance of $R^{13}$ is independently optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, —CN, —$OR_a$, —$COOR_a$, —OC(O)$R_a$, —C(O)$R_a$, —C(O)$NR_bR_c$, or —$NR_bR_c$;

each instance of $R_a$ is independently hydrogen, optionally substituted alkyl, optionally substituted cycloalkyl, optionally substituted cycloalkenyl, optionally substituted heterocycloalkyl, optionally substituted heterocycloalkenyl, optionally substituted aryl, or optionally substituted heteroaryl;

each instance of $R_b$ and $R_c$ is, independently, hydrogen, optionally substituted alkyl, optionally substituted cycloalkyl, optionally substituted cycloalkenyl, optionally substituted heterocycloalkyl, optionally substituted heterocycloalkenyl, optionally substituted aryl, optionally substituted heteroaryl, an amino protecting group, or $R_b$ and $R_c$, together with the nitrogen atom to which they are bonded are an optionally substituted heterocycloalkyl, an optionally substituted heterocycloalkenyl, or an optionally substituted heteroaryl; and q is 0, 1, 2, 3, or 4.

In certain embodiments of Formula (VI), each instance of $R^{11}$ and $R^{12}$, independently, is hydrogen, optionally substituted alkyl, —$NR_bR_c$, or —$OR_a$.

In certain embodiments of Formula (VI), $R^{11}$ is hydrogen.

In certain embodiments of Formula (VI), $R^{12}$ is optionally substituted alkyl, e.g., alkyl optionally substituted with one or more acyl or —$NR_dR_e$ groups, wherein each instance of $R_d$ and $R_e$, independently, is hydrogen, optionally substituted aryl, or optionally substituted heteroaryl. In certain embodiments of Formula (VI), $R^{12}$ is —$CH_2NHR_e$, wherein $R_e$ is optionally substituted aryl or optionally substituted heteroaryl. In certain embodiments of Formula (VI), $R_e$ is optionally substituted aryl, e.g., a monosubstituted phenyl. However, in certain embodiments, $R_e$ is unsubstituted aryl, e.g., —$C_6H_5$. In certain embodiments of Formula (VI), $R^{12}$ is —$CH(COCH_3)_2$.

In certain embodiments of Formula (VI), $R^{11}$ and $R^{12}$, together with the carbon atoms to which they are bonded form an optionally substituted heterocycloalkyl, optionally substituted heterocycloalkenyl, optionally substituted aryl, or optionally substituted heteroaryl ring.

In certain embodiments of Formula (VI), $R^{11}$ and $R^{12}$, together with the carbon atoms to which they are bonded form an optionally substituted heterocycloalkenyl ring, e.g., an optionally substituted 3,4-dihydro-pyrrol-2-one ring.

In certain embodiments of Formula (VI), wherein ----- represents a double bond, $R^{11}$ and $R^{12}$, together with the carbon atoms to which they are bonded form an optionally substituted aryl ring, e.g., an optionally substituted phenyl ring. In certain embodiments, the phenyl ring is unsubstituted.

In certain embodiments of Formula (VI), $R^{11}$ and $R^{12}$, together with the carbon atoms to which they are bonded form an optionally substituted heteroaryl ring, e.g., an optionally substituted 5-membered heteroaryl or an optionally substituted 6-membered heteroaryl ring. In certain embodiments of Formula (VI), $R^{11}$ and $R^{12}$, together with the carbon atoms to which they are bonded form an optionally substituted 5-membered heteroaryl ring, e.g., a 1,2,3-triazole ring.

In certain embodiments of Formula (VI), q is 0 and there is no $R^{13}$ substituent. In certain embodiments of Formula (VI), q is 1. In certain embodiments of Formula (VI), q is 2. In certain embodiments of Formula (VI), q is 3. In certain embodiments of Formula (VI), q is 4. In certain embodiments of Formula (VI), each instance of $R^{13}$ is independently selected from the group consisting of halo, nitro, —CN, —$OR_a$, —$COOR_a$, —$OC(O)R_a$, —$C(O)R_a$, —$C(O)NR_bR_c$, or —$NR_bR_c$. In certain embodiments of Formula (VI), q is 1 and $R^{13}$ is —$NR_bR_c$. In certain embodiments of Formula (VI), q is 1 and $R^{13}$ is nitro.

In certain embodiments, the compound of Formula (VI) is selected from any one of the compounds, or pharmaceutically acceptable salts thereof, depicted in Table 9 of the Examples.

Compounds of Formula (VII)

In another aspect, the present invention provides a compound of Formula (VII), e.g., for example, a compound for use in the treatment of a tuberculosis infection:

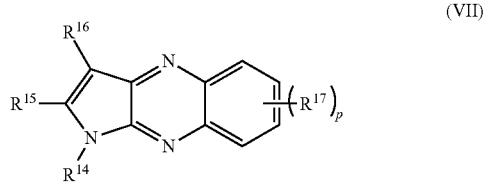

(VII)

or a pharmaceutically acceptable salt thereof;
wherein:
$R^{14}$ is optionally substituted alkyl, optionally substituted alkenyl, optionally substituted alkynyl, optionally substituted cycloalkyl, optionally substituted cycloalkenyl, heterocycloalkyl, optionally substituted heterocycloalkenyl, optionally substituted aryl, optionally substituted heteroaryl, or an amino protecting group;

each instance of $R^{15}$, $R^{16}$, and $R^{17}$, is independently, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, —CN, —$OR_a$, —$COOR_a$, —$OC(O)R_a$, —$C(O)R_a$, —$C(O)NR_bR_c$, —$NR_bR_c$, —$NR_bC(O)R_c$, or —$NR_bSO_2R_c$;

each instance of $R_a$ is independently hydrogen, optionally substituted alkyl, optionally substituted cycloalkyl, optionally substituted cycloalkenyl, optionally substituted heterocycloalkyl, optionally substituted heterocycloalkenyl, optionally substituted aryl, or optionally substituted heteroaryl;

each instance of $R_b$ and $R_c$ is, independently, hydrogen, optionally substituted alkyl, optionally substituted cycloalkyl, optionally substituted cycloalkenyl, optionally substituted heterocycloalkyl, optionally substituted heterocycloalkenyl, optionally substituted aryl, optionally substituted heteroaryl, an amino protecting group, or $R_b$ and $R_c$, together with the nitrogen atom to which they are bonded are an optionally substituted heterocycloalkyl, an optionally substituted heterocycloalkenyl, or an optionally substituted heteroaryl; and p is 0, 1, 2, 3, or 4.

In certain embodiments of Formula (VII), $R^{14}$ is optionally substituted alkyl, optionally substituted alkenyl, optionally substituted aryl, or optionally substituted heteroaryl.

In certain embodiments of Formula (VII), $R^{14}$ is optionally substituted alkyl, e.g., optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. In certain embodiments of Formula (VII), $R^{14}$ is an unsubstituted alkyl group, e.g., in certain embodiments, $R^{14}$ is —$CH_3$, —$CH_2CH_3$, —$CH_2CH_2CH_3$, —$CH_2CH_2CH_2CH_3$, —$CH_2CH_2CH_2CH_2CH_3$, —$CH(CH_3)_2$, or —$CH(CH_3)(CH_2CH_3)$. However, in certain embodiments of Formula (VII), $R^{14}$ is a substituted alkyl group, e.g., in certain embodiments, $R^{14}$ is optionally substituted aralkyl, e.g., optionally substituted aryl-$C_1$alkyl (e.g., optionally substituted benzyl) or optionally substituted aryl-$C_2$alkyl. In certain embodiments of Formula (VII), $R^{14}$ is optionally substituted heteroarylalkyl, e.g., optionally substituted heteroaryl-$C_1$alkyl or optionally substituted heteroaryl-$C_2$alkyl. In certain embodiments of Formula (VII), $R^{14}$ is alkyl substituted with one or more alkoxy substituents, e.g., $R^{14}$ is —$CH_2OCH_3$, —$CH_2CH_2OCH_3$, or —$CH_2CH_2CH_2OCH_3$.

In certain embodiments of Formula (VII), $R^{14}$ is optionally substituted alkenyl, e.g., optionally substituted $C_2$ alkenyl, optionally substituted $C_3$ alkenyl, optionally substituted $C_4$ alkenyl, optionally substituted $C_5$ alkenyl, or optionally substituted $C_6$ alkenyl. In certain embodiments of Formula (VII), $R^3$ is an unsubstituted alkenyl group, e.g., in certain embodiments, $R^{14}$ is —$CH_2CH=CH_2$. However, in certain embodiments of Formula (VII), $R^{14}$ is a substituted alkenyl group, e.g., in certain embodiments, $R^{14}$ is optionally substituted arylalkenyl, e.g., optionally substituted aryl-$C_2$alkenyl (e.g., $C_6H_5$—$C_2$alkenyl). In certain embodiments, $R^{14}$ is optionally substituted heteroarylalkenyl, e.g., optionally substituted heteroaryl-$C_2$alkenyl.

In certain embodiments, $R^{15}$ is —$NR_bR_c$, —$NR_bC(O)R_c$, or —$NR_bSO_2R_c$. In certain embodiments, $R^{15}$ is —$NR_bR_c$, e.g., —$NH_2$. In certain embodiments, $R^{15}$ is —$NR_bC(O)R_c$, e.g., —$NHC(O)R_c$ wherein $R_c$ is optionally substituted aryl or optionally substituted heteroaryl. In certain embodiments, $R^{15}$ is —$NR_bSO_2R_c$, e.g., —$NHSO_2R_c$ wherein $R_c$ is optionally substituted aryl or optionally substituted heteroaryl.

In certain embodiments of Formula (VII), $R^{16}$ is —CN, —$COOR_a$, —$C(O)R_a$, or —$C(O)NR_bR_c$. In certain embodiments of Formula (VII), $R^{16}$ is —CN. In certain embodiments of Formula (VII), $R^{16}$ is —$COOR_a$, e.g., —$COOCH_3$ or —$COOCH_2CH_3$. In certain embodiments of Formula (VII), $R^{16}$ is —$C(O)R_a$. In certain embodiments of Formula (VII), $R^{16}$ is —$C(O)NR_bR_c$, e.g., —$C(O)NHR_c$, wherein $R_c$ is optionally substituted alkyl, e.g., optionally substituted benzyl or optionally substituted $C_{1-6}$alkyl.

In certain embodiments of Formula (VII), p is 0 and there is no $R^{17}$ substituent. In certain embodiments of Formula (VII), p is 1. In certain embodiments of Formula (VII), p is 2. In certain embodiments of Formula (VII), p is 3. In certain embodiments of Formula (VII), p is 4.

In certain embodiments, the compound of Formula (VII) is selected from any one of the compounds, or pharmaceutically acceptable salts thereof, depicted in Table 10 of the Examples.

Compounds of Formula (VIII)

In another aspect, the present invention provides a compound of Formula (VIII), e.g., for example, a compound for use in the treatment of a tuberculosis infection:

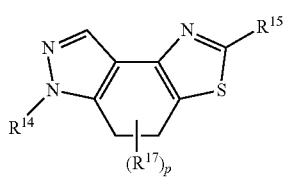

(VIII)

or a pharmaceutically acceptable salt thereof;
wherein:
$R^{14}$ is optionally substituted alkyl, optionally substituted alkenyl, optionally substituted alkynyl, optionally substituted cycloalkyl, optionally substituted cycloalkenyl, heterocycloalkyl, optionally substituted heterocycloalkenyl, optionally substituted aryl, optionally substituted heteroaryl, or an amino protecting group;
each instance of $R^{15}$ and $R^{17}$, is independently, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, —CN, —$OR_a$, —$COOR_a$, —$OC(O)R_a$, —$C(O)R_a$, —$C(O)NR_bR_c$, —$NR_bR_c$, —$NR_bC(O)R_c$, or —$NR_bSO_2R_c$;
each instance of $R_a$ is independently hydrogen, optionally substituted alkyl, optionally substituted cycloalkyl, optionally substituted cycloalkenyl, optionally substituted heterocycloalkyl, optionally substituted heterocycloalkenyl, optionally substituted aryl, or optionally substituted heteroaryl;
each instance of $R_b$ and $R_c$ is, independently, hydrogen, optionally substituted alkyl, optionally substituted cycloalkyl, optionally substituted cycloalkenyl, optionally substituted heterocycloalkyl, optionally substituted heterocycloalkenyl, optionally substituted aryl, optionally substituted heteroaryl, an amino protecting group, or $R_b$ and $R_c$, together with the nitrogen atom to which they are bonded are an optionally substituted heterocycloalkyl, an optionally substituted heterocycloalkenyl, or an optionally substituted heteroaryl; and
p is 0, 1, 2, 3, or 4.

In certain embodiments of Formula (VIII), $R^{14}$ is optionally substituted alkyl, optionally substituted alkenyl, optionally substituted aryl, or optionally substituted heteroaryl. In certain embodiments of Formula (VIII), $R^{14}$ is optionally substituted alkyl, e.g., optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. In certain embodiments of Formula (VIII), $R^{14}$ is an unsubstituted alkyl group, e.g., in certain embodiments, $R^{14}$ is —$CH_3$, —$CH_2CH_3$, or —$CH_2CH_2CH_3$.

In certain embodiments of Formula (VIII), $R^{15}$ is —$NR_bR_c$, —$NR_bC(O)R_c$, or —$NR_bSO_2R_c$. In certain embodiments of Formula (VIII), $R^{15}$ is —$NR_bC(O)R_c$, wherein $R_b$ is optionally substituted alkyl and $R_c$ is optionally substituted cycloalkyl, optionally substituted heterocycloalkyl, optionally substituted aralkyl, optionally substituted heteroarylalkyl, optionally substituted aryl, or optionally substituted heteroaryl.

In certain embodiments of Formula (VIII), p is 0 and there is no $R^{17}$ substituent. In certain embodiments of Formula (VIII), p is 1. In certain embodiments of Formula (VIII), p is 2. In certain embodiments of Formula (VIII), p is 3. In certain embodiments of Formula (VIII), p is 4.

In certain embodiments, the compound of Formula (VIII) is selected from any one of the compounds, or pharmaceutically acceptable salts thereof, depicted in Table 11 of the Examples.

Compounds of Formula (IX), (X) and (XI)

In yet another aspect, the present invention provides a compound of Formula (IX), e.g., for example, a compound for use in the treatment of a tuberculosis infection:

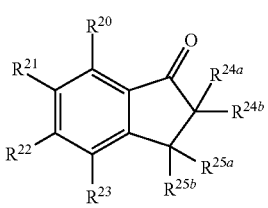

(IX)

or a pharmaceutically acceptable salt thereof;
wherein:
each instance of $R^{20}$, $R^{21}$, $R^{22}$, and $R^{23}$ is, independently, hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, or optionally substituted heteroaryl, halo, nitro, —CN, —$OR_a$, —$COOR_a$, —$OC(O)R_a$, —$C(O)R_a$, —$C(O)NR_bR_c$, or —$NR_bR_c$;
each instance of $R^{24a}$, $R^{24b}$, $R^{25a}$, and $R^{25b}$ is, independently, hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, or optionally substituted heteroaryl, halo, nitro, —CN, —OR$_a$, —COOR$_a$, —OC(O)R$_a$, —C(O)R$_a$, —C(O)NR$_b$R$_c$, or —NR$_b$R$_c$; or R$^{24a}$ and R$^{25a}$ are absent, and R$^{24b}$ and R$^{25b}$ together with the carbon atom to which they are attached form an optionally substituted aryl or optionally substituted heteroaryl ring; or R$^{24a}$ and R$^{24b}$ together with the carbon atom to which they are attached form a =C—R$_a$ group;

each instance of R$_a$ is independently hydrogen, optionally substituted alkyl, optionally substituted cycloalkyl, optionally substituted cycloalkenyl, optionally substituted heterocycloalkyl, optionally substituted heterocycloalkenyl, optionally substituted aryl, or optionally substituted heteroaryl; and each instance of R$_b$ and R$_c$ is, independently, hydrogen, optionally substituted alkyl, optionally substituted cycloalkyl, optionally substituted cycloalkenyl, optionally substituted heterocycloalkyl, optionally substituted heterocycloalkenyl, optionally substituted aryl, optionally substituted heteroaryl, an amino protecting group, or R$_b$ and R$_c$, together with the nitrogen atom to which they are bonded are an optionally substituted heterocycloalkyl, an optionally substituted heterocycloalkenyl, or an optionally substituted heteroaryl.

In certain embodiments of Formula (IX), R$^{20}$ is hydrogen. In certain embodiments Formula (IX), R$^{21}$ is hydrogen. In certain embodiments Formula (IX), R$^{22}$ is hydrogen. In certain embodiments Formula (IX), R$^{23}$ is hydrogen. In certain embodiments Formula (IX), each instance of R$^{20}$, R$^{21}$ and R$^{23}$ is hydrogen.

In certain embodiments Formula (IX), R$^{24a}$ and R$^{24b}$ are hydrogen. In certain embodiments Formula (IX), R$^{25a}$ and R$^{25b}$ are hydrogen.

In certain embodiments Formula (IX), R$^{24a}$ is —OR$_a$. In certain embodiments Formula (IX), R$^{24b}$ is —OR$_a$. In certain embodiments Formula (IX), R$^{25a}$ is —OR$_a$. In certain embodiments Formula (IX), R$^{25b}$ is —OR$_a$. In certain embodiments Formula (IX), each instance of R$^{24a}$, R$^{25a}$, and R$^{25b}$ is independently —OR$_a$, e.g., —OH. In this instance, in certain embodiments, R$^{24b}$ is an optionally substituted heterocycloalkenyl.

In certain embodiments of Formula (IX), R$^{24a}$ and R$^{24b}$ together with the carbon atom to which they are attached form a =C—R$_a$ group. In this instance, in certain embodiments, R$_a$ is optionally substituted aryl or optionally substituted heteroaryl.

In certain embodiments of Formula (IX), R$^{24a}$ and R$^{25a}$ are absent, and R$^{24b}$ and R$^{25b}$ together with the carbon atom to which they are attached form an optionally substituted aryl or optionally substituted heteroaryl.

In certain embodiments of Formula (IX), R$^{24a}$ and R$^{25a}$ are absent, and R$^{24b}$ and R$^{25b}$ together with the carbon atom to which they are attached form an optionally substituted heteroaryl, e.g., a 5,6- or 6,6-fused bicyclic heteroaryl ring system. In certain embodiments, the hetoaryl ring is substituted. However, in certain embodiments, the hetoaryl ring is unsubstituted. In certain embodiments of Formula (IX), R$^{24b}$ and R$^{25b}$ together with the carbon atom to which they are attached form an optionally substituted 5,6-fused bicyclic heteroaryl ring system, e.g., [1,2,3]triazolo[4,5-b]pyrazinyl, [1,2,5]oxadiazolo[3,4-b]pyrazinyl, or [1,2,5]thiadiazolo[3,4-b]pyrazinyl. In certain embodiments of Formula (IX), R$^{24b}$ and R$^{25b}$ together with the carbon atom to which they are attached form a [1,2,5]oxadiazolo[3,4-b]pyrazinyl ring.

In certain embodiments, the compound of Formula (IX) is selected from any one of the compounds, or pharmaceutically acceptable salts thereof, depicted in Table 1 of the Examples.

In yet another aspect, the present invention provides a compound of Formula (X), e.g., for example, a compound for use in the treatment of a tuberculosis infection:

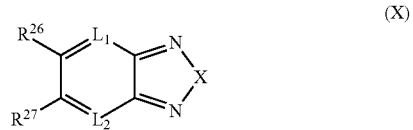

(X)

or a pharmaceutically acceptable salt thereof;
wherein:

each instance of R$^{26}$ and R$^{27}$ is, independently, hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, or optionally substituted heteroaryl, halo, nitro, —CN, —OR$_a$, —COOR$_a$, —OC(O)R$_a$, —C(O)R$_a$, —C(O)NR$_b$R$_c$, or —NR$_b$R$_c$, or R$^{26}$ and R$^{27}$ together with the carbon atoms to which they are bonded form an optionally substituted cycloalkyl, optionally substituted cycloalkenyl, optionally substituted heterocycloalkyl, optionally substituted heterocycloalkenyl, optionally substituted aryl, or optionally substituted heteroaryl ring;

each instance of L$_1$ and L$_2$ is independently —N— or —C(R$^{28}$)—, wherein R$^{28}$ is, independently, hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, or optionally substituted heteroaryl, halo, nitro, —CN, —OR$_a$, —COOR$_a$, —OC(O)R$_a$, —C(O)R$_a$, —C(O)NR$_b$R$_c$, or —NR$_b$R$_c$;

X is —O—, —S—, or —N(R$_b$)—;

each instance of R$_a$ is independently hydrogen, optionally substituted alkyl, optionally substituted cycloalkyl, optionally substituted cycloalkenyl, optionally substituted heterocycloalkyl, optionally substituted heterocycloalkenyl, optionally substituted aryl, or optionally substituted heteroaryl; and each instance of R$_b$ and R$_c$ is, independently, hydrogen, optionally substituted alkyl, optionally substituted cycloalkyl, optionally substituted cycloalkenyl, optionally substituted heterocycloalkyl, optionally substituted heterocycloalkenyl, optionally substituted aryl, optionally substituted heteroaryl, an amino protecting group, or R$_b$ and R$_c$, together with the nitrogen atom to which they are bonded are an optionally substituted heterocycloalkyl, an optionally substituted heterocycloalkenyl, or an optionally substituted heteroaryl.

In certain embodiments of Formula (X), X is —O—. In certain embodiments of Formula (X), X is —S—. In certain embodiments of Formula (X), X is —N(R$_b$)—.

In certain embodiments of Formula (X), each instance of L$_1$ and L$_2$ is —C(R$^{28}$)—. In this instance, in certain embodiments, each instance of R$^{26}$ and R$^{27}$ is, independently, hydrogen, halo, —OR$_a$, or —NR$_b$R$_c$. In this instance, in certain embodiments, each instance of R$^{28}$ is independently hydrogen, halo, —OR$_a$, or —NR$_b$R$_c$.

In certain embodiments of Formula (X), each instance of L$_1$ and L$_2$ is —N—. In this instance, in certain embodiments, R$^{26}$ and R$^{27}$ together with the carbon atoms to which they are bonded form an optionally substituted cycloalkyl, optionally substituted cycloalkenyl, optionally substituted heterocycloalkyl, optionally substituted heterocycloalkenyl, optionally substituted aryl, or optionally substituted heteroaryl ring. In this instance, in certain embodiments, $R^{26}$ and $R^{27}$ together with the carbon atoms to which they are bonded form an optionally substituted cycloalkenyl ring.

In certain embodiments, the compound of Formula (X) is selected from any one of the compounds, or pharmaceutically acceptable salts thereof, depicted in Table 2 of the Examples.

In certain embodiments, the compound of the present invention is encompassed by both Formulae (IX) and (X), e.g., for example, a compound of Formula (XI):

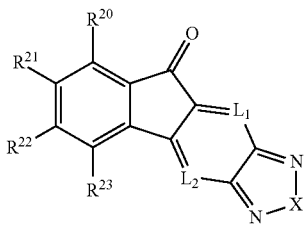

(XI)

or a pharmaceutically acceptable salt thereof;
wherein $L_1$, $L_2$, X, $R^{20}$, $R^{21}$, $R^{22}$, $R^{23}$, are as defined above for Formulae (IX) and (X)

In certain embodiments of Formula (XI), each instance of $R^{20}$, $R^{21}$, $R^{22}$, and $R^{23}$ is hydrogen. In certain embodiments of Formula (XI), X is —O—. In certain embodiments of Formula (XI), each instance of $L_1$ and $L_2$ is —N—.

In certain embodiments of Formula (XI), the compound is:

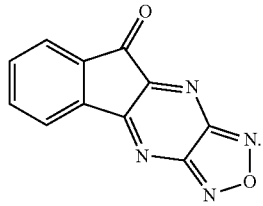 [SMILES: O=C1c2ccccc2-c2nc3nonc3nc21]

However, in certain embodiments, this compound is specifically excluded.

Compounds of Formula (XII) and (XIII)

In still yet another aspect, the present invention provides a compound of Formula (XII), e.g., for example, a compound for use in the treatment of a tuberculosis infection:

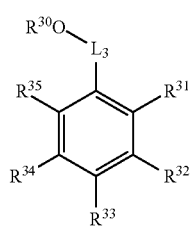

(XII)

or a pharmaceutically acceptable salt thereof;

wherein:

$R^{30}$ is optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, or optionally substituted heteroaryl, —COOR$_a$, —C(O)R$_a$, or —C(O)NR$_b$R$_c$;

$L_3$ is a bond or optionally substituted alkylene;

each instance of $R^{31}$, $R^{32}$, $R^{33}$, $R^{34}$, and $R^{35}$ is, independently, hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, or optionally substituted heteroaryl, halo, nitro, —CN, —OR$_a$, —COOR$_a$, —OC(O)R$_a$, —C(O)R$_a$, —C(O)NR$_b$R$_c$, or —NR$_b$R$_c$;

each instance of R$_a$ is independently hydrogen, optionally substituted alkyl, optionally substituted cycloalkyl, optionally substituted cycloalkenyl, optionally substituted heterocycloalkyl, optionally substituted heterocycloalkenyl, optionally substituted aryl, or optionally substituted heteroaryl; and each instance of R$_b$ and R$_c$ is, independently, hydrogen, optionally substituted alkyl, optionally substituted cycloalkyl, optionally substituted cycloalkenyl, optionally substituted heterocycloalkyl, optionally substituted heterocycloalkenyl, optionally substituted aryl, optionally substituted heteroaryl, an amino protecting group, or R$_b$ and R$_c$, together with the nitrogen atom to which they are bonded are an optionally substituted heterocycloalkyl, an optionally substituted heterocycloalkenyl, or an optionally substituted heteroaryl.

In certain embodiments, $R^{30}$ is optionally substituted alkyl, optionally substituted alkenyl, or —C(O)R$_a$, wherein R$_a$ is optionally substituted alkyl, optionally substituted cycloalkyl, optionally substituted cycloalkenyl, optionally substituted heterocycloalkyl, optionally substituted heterocycloalkenyl, optionally substituted aryl, or optionally substituted heteroaryl.

In certain embodiments, $L_3$ is a bond. In certain embodiments, $L_3$ is an optionally substituted $C_{1-6}$ alkylene, e.g., optionally substituted $C_1$ alkylene, optionally substituted $C_2$ alkylene, optionally substituted $C_3$ alkylene, optionally substituted $C_4$ alkylene, optionally substituted $C_5$ alkylene, or optionally substituted $C_6$ alkylene. In certain embodiments, the alkylene group is substituted. In other embodiments, the alkylene group is unsubstituted, e.g., wherein $L_3$ is —CH$_2$— or —CH$_2$CH$_2$—.

In certain embodiments, $R^{31}$, $R^{32}$, $R^{33}$, $R^{34}$, $R^{35}$ are each hydrogen, thus providing a monosubstituted phenyl ring. In this instance, in certain embodiments, $R^{30}$ is optionally substituted alkenyl, e.g., optionally substituted C$_2$alkenyl, optionally substituted C$_3$alkenyl, optionally substituted C$_4$alkenyl, optionally substituted C$_5$alkenyl, or optionally substituted C$_6$alkenyl. In certain embodiments, $R^{30}$ is —CH$_2$—CH=CH$_2$.

In certain embodiments, $R^{32}$, $R^{33}$, $R^{34}$, and $R^{35}$ are hydrogen, thus, in certain embodiments, providing a 1,2-disubstituted phenyl ring.

In certain embodiments, $R^{31}$, $R^{33}$, $R^{34}$, and $R^{35}$ are hydrogen, thus, in certain embodiments, providing a 1,3-disubstituted phenyl ring.

In other embodiments, $R^{31}$, $R^{32}$, $R^{34}$, and $R^{35}$ are hydrogen, thus, in certain embodiments, providing a 1,4-disubstituted phenyl ring. In this instance, in certain embodiments, $R^{30}$ is optionally substituted alkyl, e.g., optionally substituted $C_1$ alkyl, optionally substituted $C_2$ alkyl, optionally substituted $C_3$ alkyl, optionally substituted $C_4$ alkyl, optionally substituted $C_5$ alkyl, or optionally substituted $C_6$ alkyl. In certain embodiments, $R^{30}$ is —$CH_3$. Furthermore, in this instance, in certain embodiments, $R^{33}$ is optionally substituted alkyl, e.g., optionally substituted $C_1$ alkyl, optionally substituted $C_2$ alkyl, optionally substituted $C_3$ alkyl, optionally substituted $C_4$ alkyl, optionally substituted $C_5$ alkyl, or optionally substituted $C_6$ alkyl. In certain embodiments, $R^{30}$ is —$CH_2CH_2I$, —$CH_2CH_2Br$, —$CH_2CH_2Cl$, or —$CH_2CH_2F$.

In yet other embodiments, $R^{31}$ and $R^{33}$ are hydrogen, thus, in certain embodiments, providing a 1,2,3,5-tetrasubstituted phenyl ring. In this instance, in certain embodiments, $R^{32}$, $R^{34}$, and $R^{35}$ are each substituents selected from the group consisting of —$OR_a$, —$COOR_a$, —$OC(O)R_a$, —$C(O)R_a$, —$C(O)NR_bR_c$, or —$NR_bR_c$. In certain embodiments, each instance of $R^{34}$ and $R^{35}$ is independently —$OR_a$, e.g., —OH. In certain embodiments, $R^{32}$ is —$COOR_a$, e.g., wherein in certain embodiments, $R_a$ is optionally substituted heterocycloalkyl. In certain embodiments, —$COOR_a$ is a prodrug ester group, e.g., an ester which may be hydrolyzed in vivo to —$CO_2H$.

In certain embodiments, the compound of Formula (XII) is selected from any one of the compounds, or pharmaceutically acceptable salts thereof, depicted in Table 3 of the Examples.

In certain embodiments, the compound of Formula (XII) is of Formula (XIII):

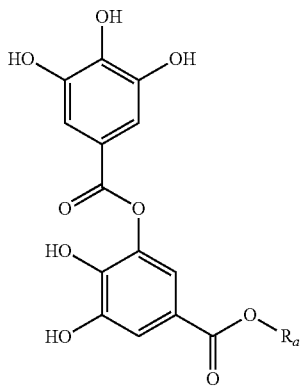

(XIII)

or a pharmaceutically acceptable salt thereof; wherein $R_a$ is hydrogen, optionally substituted alkyl, optionally substituted cycloalkyl, optionally substituted cycloalkenyl, optionally substituted heterocycloalkyl, optionally substituted heterocycloalkenyl, optionally substituted aryl, or optionally substituted heteroaryl. In certain embodiments, $R_a$ is optionally substituted heterocycloalkyl, e.g., a optionally substituted 6-membered heterocycloalkyl such as a monosaccharide.

In certain embodiments, the compound of Formula (XIII) is:

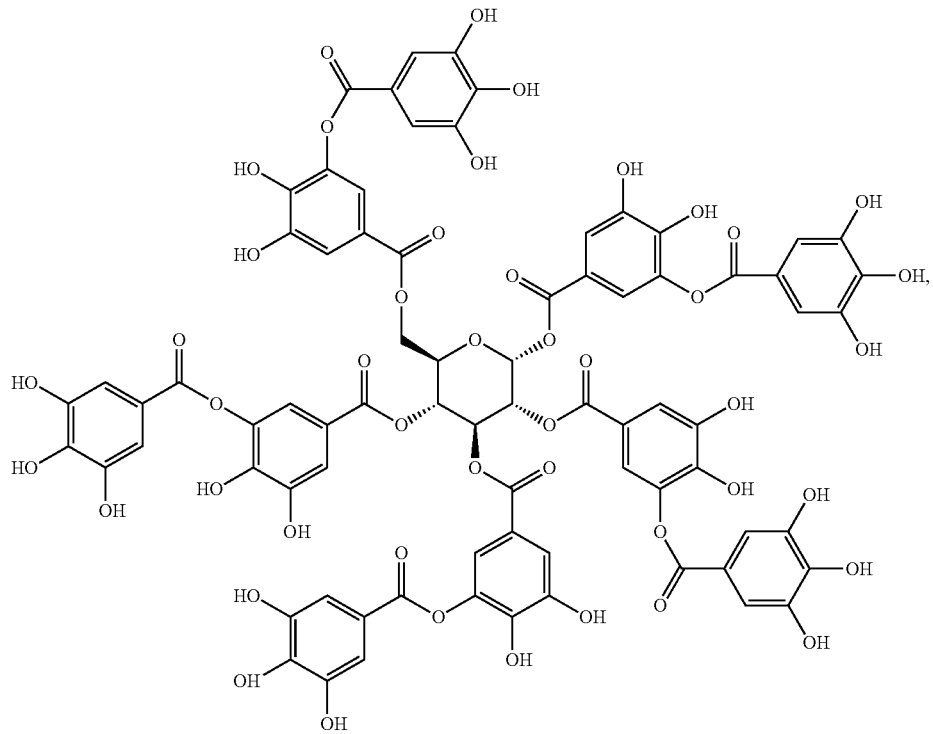 [SMILES: O=C(OC[C@H]1O[C@H](OC(=O)c2cc(O)c(O)c(OC(=O)c3cc(O)c(O)c(O)c3)c2)[C@H](OC(=O)c2cc(O)c(O)c(OC(=O)c3cc(O)c(O)c(O)c3)c2)[C@@H](OC(=O)c2cc(O)c(O)c(OC(=O)c3cc(O)c(O)c(O)c3)c2)[C@@H]1OC(=O)c1cc(O)c(O)c(OC(=O)c2cc(O)c(O)c(O)c2)c1)c1cc(O)c(O)c(OC(=O)c2cc(O)c(O)c(O)c2)c1]

or pharmaceutically acceptable salt thereof.

Compounds of Formula (XIV)

In still yet another aspect, the present invention provides a compound of Formula (XIV), e.g., for example, a compound for use in the treatment of a tuberculosis infection:

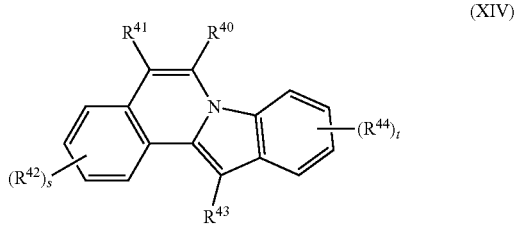

or a pharmaceutically acceptable salt thereof;
wherein:

each instance of $R^{40}$, $R^{41}$, and $R^{43}$, is, independently, hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, or optionally substituted heteroaryl, halo, nitro, —CN, —$OR_a$, —$COOR_a$, —OC(O)$R_a$, —C(O)$R_a$, —C(O)$NR_bR_c$, or —$NR_bR_c$;

each instance of $R^{42}$ and $R^{44}$, is, independently, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, or optionally substituted heteroaryl, halo, nitro, —CN, —$OR_a$, —$COOR_a$, —OC(O)$R_a$, —C(O)$R_a$, —C(O)$NR_bR_c$, or —$NR_bR_c$;

each instance of $R_a$ is independently hydrogen, optionally substituted alkyl, optionally substituted cycloalkyl, optionally substituted cycloalkenyl, optionally substituted heterocycloalkyl, optionally substituted heterocycloalkenyl, optionally substituted aryl, or optionally substituted heteroaryl;

each instance of $R_b$ and $R_c$ is, independently, hydrogen, optionally substituted alkyl, optionally substituted cycloalkyl, optionally substituted cycloalkenyl, optionally substituted heterocycloalkyl, optionally substituted heterocycloalkenyl, optionally substituted aryl, optionally substituted heteroaryl, an amino protecting group, or $R_b$ and $R_c$, together with the nitrogen atom to which they are bonded are an optionally substituted heterocycloalkyl, an optionally substituted heterocycloalkenyl, or an optionally substituted heteroaryl;

s is 0, 1, 2, 3, or 4; and
t is 0, 1, 2, 3, or 4.

In certain embodiments of Formula (XIV), $R^{40}$ is hydrogen. In certain embodiments of Formula (XIV), $R^{41}$ is hydrogen. In certain embodiments of Formula (XIV), $R^{43}$ is hydrogen. In certain embodiments of Formula (XIV), each instance of $R^{40}$, $R^{41}$, and $R^{43}$ is hydrogen.

In certain embodiments of Formula (XIV), s is 0 and there is no $R^{42}$ substituent. In certain embodiments of Formula (XIV), s is 1. In certain embodiments of Formula (XIV), s is 2. In certain embodiments of Formula (VIII), s is 3. In certain embodiments of Formula (XIV), s is 4.

In certain embodiments of Formula (XIV), t is 0 and there is no $R^{44}$ substituent. In certain embodiments of Formula (XIV), t is 1. In certain embodiments of Formula (XIV), t is 2. In certain embodiments of Formula (VIII), t is 3. In certain embodiments of Formula (XIV), t is 4.

In certain embodiments, the compound is:

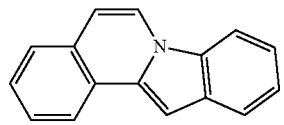 [SMILES: c1ccc2c(c1)ccn1c3ccccc3cc21]

or a pharmaceutically acceptable salt thereof.

Compounds of Formula (XV), (III), and (IV)

In still yet another aspect, the present invention provides a compound of Formula (XV), e.g., for example, a compound for use in the treatment of a tuberculosis infection:

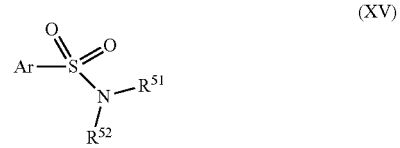

or a pharmaceutically acceptable salt thereof;
wherein:

Ar is an optionally substituted aryl or optionally substituted heteroaryl;

$R^{51}$ is hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, or an amino protecting group; and $R^{52}$ is optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, or an amino protecting group; or $R^{51}$ and $R^{52}$, together with the nitrogen atom to which they are attached form an optionally substituted heterocycloalkyl or optionally substituted heterocycloalkenyl ring.

In certain embodiments of Formula (XV), Ar is an optionally substituted aryl, e.g., optionally substituted phenyl. In certain embodiments of Formula (XV), optionally substituted heteroaryl. In certain embodiments of Formula (XV), Ar is a 5-membered optionally substituted heteroaryl ring, e.g., optionally substituted imidazolyl. In certain embodiments of Formula (XV), Ar is a 6-membered optionally substituted heteroaryl ring, e.g., optionally substituted pyridinyl.

In certain embodiments of Formula (XV), $R^{51}$ and $R^{52}$, together with the nitrogen atom to which they are attached form an optionally substituted heterocycloalkyl ring, e.g., an optionally substituted piperidinyl ring.

However, in certain embodiments of Formula (XV), $R^{51}$ is hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, or an amino protecting group; and $R^{52}$ is optionally substituted alkyl, e.g., —$CH_2C(=O)N(R^7)(R^8)$, wherein each instance of $R^7$ and $R^8$, independently, is hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, or optionally substituted heteroaryl. Other more specific embodiments of $R^7$ and $R^8$ are described below and herein for compounds of Formulae (III) and (IV) and which are further encompassed by Formula (XV). In certain embodiments of Formula (XV), $R^{51}$ is hydrogen. In certain embodiments of Formula (XV), $R^{51}$ is optionally substituted alkyl, e.g., optionally substituted $C_1$alkyl, optionally substituted $C_2$ alkyl, optionally substituted $C_3$ alkyl, optionally substituted $C_4$ alkyl, optionally substituted $C_5$ alkyl, or optionally substituted $C_6$ alkyl. In certain embodiments, $R^{51}$ is —$CH_3$.

In certain embodiments, the compound of Formula (XV) is selected from any one of the compounds, or pharmaceutically acceptable salts thereof, depicted in Table 5 of the Examples.

In certain embodiments of Formula (XV), the compound is of Formula (III):

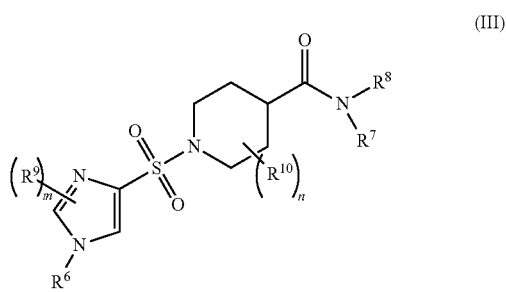

(III)

or a pharmaceutically acceptable salt thereof;
wherein:
each of $R^6$, $R^7$, and $R^8$, independently, is H, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, or optionally substituted heteroaryl;

each of $R^9$ and $R^{10}$, independently, is optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, —CN, —$OR_a$, —$COOR_a$, —$OC(O)R_a$, —$C(O)R_a$, —$C(O)NR_bR_c$, or —$NR_bR_c$;

each instance of $R_a$ is independently hydrogen, optionally substituted alkyl, optionally substituted cycloalkyl, optionally substituted cycloalkenyl, optionally substituted heterocycloalkyl, optionally substituted heterocycloalkenyl, optionally substituted aryl, or optionally substituted heteroaryl;

each instance of $R_b$ and $R_c$ is, independently, hydrogen, optionally substituted alkyl, optionally substituted cycloalkyl, optionally substituted cycloalkenyl, optionally substituted heterocycloalkyl, optionally substituted heterocycloalkenyl, optionally substituted aryl, optionally substituted heteroaryl, an amino protecting group, or $R_b$ and $R_c$, together with the nitrogen atom to which they are bonded are an optionally substituted heterocycloalkyl, an optionally substituted heterocycloalkenyl, or an optionally substituted heteroaryl;

m is 0, 1, or 2; and
n is 0, 1, 2, 3, 4, 5, 6, 7, 8, or 9.

In certain embodiments of Formula (III), $R^7$ is hydrogen.

In certain embodiments of Formula (III), $R^8$ is optionally substituted alkyl, optionally substituted cycloalkyl, optionally substituted heterocycloalkyl, optionally substituted aryl, optionally substituted heteroaryl.

In certain embodiments of Formula (III), $R^8$ is optionally substituted alkyl, e.g., optionally substituted $C_1$alkyl, optionally substituted $C_2$ alkyl, optionally substituted $C_3$ alkyl, optionally substituted $C_4$ alkyl, optionally substituted $C_5$ alkyl, or optionally substituted $C_6$ alkyl. In certain embodiments of Formula (III), $R^8$ is an unsubstituted alkyl group. However, in certain embodiments of Formula (III), $R^8$ is a substituted alkyl group, e.g., in certain embodiments, $R^8$ is optionally substituted aralkyl, e.g., optionally substituted aryl-$C_1$alkyl (e.g., optionally substituted benzyl), optionally substituted aryl-$C_2$alkyl, or optionally substituted aryl-$C_3$alkyl. In certain embodiments of Formula (III), $R^8$ is optionally substituted heteroarylalkyl, e.g., optionally substituted heteroaryl-$C_1$alkyl, optionally substituted heteroaryl-$C_2$alkyl, or optionally substituted heteroaryl-$C_3$alkyl.

In certain embodiments of Formula (III), $R^8$ is optionally substituted cycloalkyl, e.g., optionally substituted $C_3$ cycloalkyl, optionally substituted $C_4$ cycloalkyl, optionally substituted $C_5$ cycloalkyl, or optionally substituted $C_6$ cycloalkyl.

In certain embodiments of Formula (III), $R^8$ is optionally substituted aryl, e.g., a monosubstituted phenyl, a disubstituted phenyl, or the phenyl ring is fused to a heterocylic ring, e.g., such as a 1,3-dioxolanyl or a 1,4-dioxanyl ring. In certain embodiments of Formula (III), $R^8$ is a monosubstituted phenyl, e.g., substituted at the ortho, meta, or para position relative to the point of attachment. In certain embodiments of Formula (III), $R^8$ is a disubstituted phenyl, e.g., substituted at the 1,2-, 1,3-, 1,4-, 1,5-, 2,3-, or 2,4-position relative to the point of attachment. In certain embodiments of Formula (III), $R^8$ is a trisubstituted phenyl, e.g., substituted at the 1,2,3-, the 2,3,5-, the 1,2,5-, the 1,2,4-, or the 1,3,5-position relative to the point of attachment. In certain embodiments of Formula (III), $R^8$ is a tetrasubstituted phenyl. In certain embodiments, the phenyl ring is substituted with at least one substituent (e.g., 1, 2, 3, or 4 substituents) selected from the group consisting of halogen (e.g., —F, —Br, —I, —Cl), alkoxy, $C_{1-4}$alkyl, sulfonamido, alkylthio, alkylamino, heteroaryl, and a carboxylic ester. However, in certain embodiments of Formula (III), the phenyl ring is unsubstituted.

In certain embodiments of Formula (III), $R^8$ is optionally substituted heteroaryl, e.g., optionally substituted 5-membered heteroaryl, optionally substituted 6-membered heteroaryl, or an optionally substituted 5,6-bicyclic heteroaryl. In certain embodiments of Formula (III), $R^8$ is optionally substituted 5-membered heteroaryl, e.g., optionally substituted thiophenyl, optionally substituted furanyl, or optionally substituted pyrrolyl. In certain embodiments of Formula (III), $R^8$ is optionally substituted 6-membered heteroaryl, e.g., optionally substituted pyridinyl. In certain embodiments of Formula (III), $R^8$ is optionally substituted 5,6-bicyclic heteroaryl, e.g., optionally substituted benzothiazolyl. In certain embodiments of Formula (III), the hetoaryl ring is substituted. However, in certain embodiments of Formula (III), the hetoaryl ring is unsubstituted.

In certain embodiments of Formula (III), $R^6$ is hydrogen. In certain embodiments of Formula (III), $R^6$ is optionally substituted alkyl, e.g., optionally substituted $C_1$alkyl, optionally substituted $C_2$ alkyl, optionally substituted $C_3$ alkyl, optionally substituted $C_4$ alkyl, optionally substituted $C_5$ alkyl, or optionally substituted $C_6$ alkyl. In certain embodiments of Formula (III), $R^6$ is —$CH_3$, —$CH_2CH_3$, or —$CH(CH_3)_2$.

In certain embodiments of Formula (III), m is 0. In certain embodiments of Formula (III), m is 1. In certain embodiments of Formula (III), m is 2.

In certain embodiments of Formula (III), n is 0. In certain embodiments of Formula (III), n is 1. In certain embodiments of Formula (III), n is 2. In certain embodiments of Formula (III), n is 3. In certain embodiments of Formula (III), n is 4. In certain embodiments of Formula (III), n is 5. In certain embodiments of Formula (III), n is 6. In certain embodiments of Formula (III), n is 7. In certain embodiments of Formula (III), n is 8. In certain embodiments of Formula (III), n is 9.

In certain embodiments of Formula (III), each of m and n is 0.

In certain embodiments of Formula (XV), the compound is of Formula (IV):

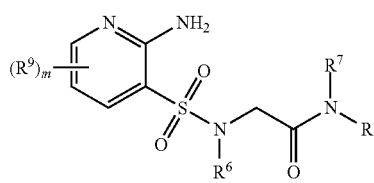

(IV)

or a pharmaceutically acceptable salt thereof;
wherein:
each of $R^6$, $R^7$, and $R^8$, independently, is H, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, or optionally substituted heteroaryl;
each of $R^9$ and $R^{10}$, independently, is optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, —CN, —$OR_a$, —$COOR_a$, —$OC(O)R_a$, —$C(O)R_a$, —$C(O)NR_bR_c$, or —$NR_bR_c$;
each instance of $R_a$ is independently hydrogen, optionally substituted alkyl, optionally substituted cycloalkyl, optionally substituted cycloalkenyl, optionally substituted heterocycloalkyl, optionally substituted heterocycloalkenyl, optionally substituted aryl, or optionally substituted heteroaryl;
each instance of $R_b$ and $R_c$ is, independently, hydrogen, optionally substituted alkyl, optionally substituted cycloalkyl, optionally substituted cycloalkenyl, optionally substituted heterocycloalkyl, optionally substituted heterocycloalkenyl, optionally substituted aryl, optionally substituted heteroaryl, an amino protecting group, or $R_b$ and $R_c$, together with the nitrogen atom to which they are bonded are an optionally substituted heterocycloalkyl, an optionally substituted heterocycloalkenyl, or an optionally substituted heteroaryl;
m is 0, 1, or 2; and
n is 0, 1, 2, 3, 4, 5, 6, 7, 8, or 9.

In certain embodiments of Formula (IV), $R^7$ is hydrogen.
In certain embodiments of Formula (IV), $R^8$ is optionally substituted aryl or optionally substituted heteroaryl.

In certain embodiments of Formula (IV), $R^8$ is optionally substituted aryl, e.g., a monosubstituted phenyl, a disubstituted phenyl, or the phenyl ring is fused to a heterocylic ring, e.g., such as a 1,3-dioxolanyl or a 1,4-dioxanyl ring. In certain embodiments of Formula (IV), $R^8$ is a monosubstituted phenyl, e.g., substituted at the ortho, meta, or para position relative to the point of attachment. In certain embodiments of Formula (IV), $R^8$ is a disubstituted phenyl, e.g., substituted at the 1,2-, 1,3-, 1,4-, 1,5-, 2,3-, or 2,4-position relative to the point of attachment. In certain embodiments of Formula (IV), $R^8$ is a trisubstituted phenyl, e.g., substituted at the 1,2,3-, the 2,3,5-, the 1,2,5-, the 1,2,4-, or the 1,3,5-position relative to the point of attachment. In certain embodiments of Formula (IV), $R^8$ is a tetrasubstituted phenyl. In certain embodiments, the phenyl ring is substituted with at least one substituent (e.g., 1, 2, 3, or 4 substituents) selected from the group consisting of halogen (e.g., —F, —Br, —I, —Cl), alkoxy, and $C_{1-4}$alkyl. However, in certain embodiments of Formula (IV), the phenyl ring is unsubstituted.

In certain embodiments of Formula (IV), $R^8$ is optionally substituted heteroaryl, e.g., optionally substituted 5-membered heteroaryl or optionally substituted 6-membered heteroaryl. In certain embodiments of Formula (IV), $R^8$ is optionally substituted 5-membered heteroaryl, e.g., optionally substituted thiophenyl, optionally substituted furanyl, or optionally substituted pyrrolyl. In certain embodiments of Formula (III), $R^8$ is optionally substituted 6-membered heteroaryl, e.g., optionally substituted pyridinyl. In certain embodiments of Formula (IV), the hetoaryl ring is substituted. However, in certain embodiments of Formula (IV), the hetoaryl ring is unsubstituted.

In certain embodiments of Formula (IV), $R^6$ is hydrogen. In certain embodiments of Formula (IV), $R^6$ is optionally substituted alkyl, e.g., optionally substituted $C_1$alkyl, optionally substituted $C_2$ alkyl, optionally substituted $C_3$ alkyl, optionally substituted $C_4$ alkyl, optionally substituted $C_5$ alkyl, or optionally substituted $C_6$ alkyl. In certain embodiments of Formula (IV), $R^6$ is —$CH_3$.

In certain embodiments of Formula (IV), m is 0. In certain embodiments of Formula (IV), m is 1. In certain embodiments of Formula (IV), m is 2. In certain embodiments of Formula (IV), m is 1 and $R^9$ is halo, e.g., —Br.

Compounds of Formula (XVI)

In still yet another aspect, the present invention provides a compound of Formula (XVI), e.g., for example, a compound for use in the treatment of a tuberculosis infection:

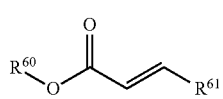

(XVI)

or a pharmaceutically acceptable salt thereof;
wherein:
$R^{60}$ is hydrogen, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, or an oxygen protecting group; and
$R^{61}$ is optionally substituted alkyl.

In certain embodiments of Formula (XVI), $R^{60}$ is optionally substituted alkyl, e.g., optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. In certain embodiments of Formula (XVI), $R^{60}$ is an unsubstituted alkyl group, e.g., in certain embodiments, $R^{60}$ is —$CH_3$, —$CH_2CH_3$, or —$CH_2CH_2CH_3$. In other embodiments of Formula (XVI), $R^{60}$ is an oxygen protecting group In certain embodiments of Formula (XVI), $R^{61}$ is optionally substituted $C_{1-6}$alkyl, e.g., optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. In certain embodiments of Formula (XVI), $R^{61}$ is an unsubstituted alkyl group, e.g., in certain embodiments, $R^{61}$ is —$CH_3$ or —$CH_2CH_3$. However, in certain embodiments of Formula (XVI), $R^{61}$ is a substituted alkyl group, e.g., in certain embodiments, $R^{61}$ is a substituted $C_1$alkyl group, e.g., —$CH_2Br$.

In certain embodiments of (XVI), the compound is:

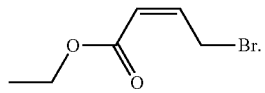

Pharmaceutical Compositions and Administration

The present invention provides pharmaceutical compositions comprising a compound of the present invention, e.g., a compound of any one of Formulae (I) to (XVI), as described herein, and a pharmaceutically acceptable excipient, e.g., for use as a medicament in treating tuberculosis. In certain embodiments, the compound of the present invention is provided in an effective amount in the pharmaceutical composition. In certain embodiments, the effective amount is a therapeutically effective amount. In certain embodiments, the effective amount is a prophylactically effective amount.

Pharmaceutically acceptable excipients include any and all solvents, diluents, or other liquid vehicles, dispersions, suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851;

5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered. by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

To practice the method of this invention, the above-described compound or its pharmaceutical composition can be administered orally, parenterally, by inhalation spray, topically, rectally, nasally, buccally, vaginally, rectally, or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually. Additional therapeutically active agents include antibiotic agents, e.g., antibiotics useful for treating tuberculosis. Exemplary antibiotics include, but are not limited to, isoniazid, rifampin, pyrazinamide, ethambutol, and streptomycin. In certain embodiments, the additional therapeutically active agent is Wu-Bei-Zi. In certain embodiments, the additional therapeutically active agent is a tuberculosis vaccine, e.g., *Bacillus* Calmette-Guerin vaccine.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Methods of Use and Treatment

As described herein, the present invention provides methods of treating a tuberculosis infection, the method comprising administering an effective amount of a compound of the present invention, e.g., a compound of Formula (I) to (XVI), as described herein, or a pharmaceutically acceptable salt thereof, or pharmaceutical composition thereof, to a subject in need thereof.

In certain embodiments, the effective amount is a therapeutically effective amount. In certain embodiments, the effective amount is a prophylactically effective amount.

In certain embodiments, the tuberculosis infection is a *Mycobacterium tuberculosis* infection. In certain embodiments, the tuberculosis infection is multi-drug-resistant tuberculosis (MDR-TB) infection, e.g., resistant to first-line TB drugs rifampicin and/or isoniazid. In certain embodiments, the tuberculosis infection is extensively-drug-resistant tuberculosis (XDR-TB) infection, e.g., also resistant to three or more of the six classes of second-line drugs (see, e.g., Centers for Disease Control and Prevention (CDC) (2006). "Emergence of *Mycobacterium tuberculosis* with extensive resistance to second-line drugs worldwide, 2000-2004". *MMWR Morb Mortal Wkly Rep* 55 (11): 301-5).

Further provided is a method for inhibiting lipoamide dehydrogenase activity, the method comprising contacting a lipoamide dehydrogenase with an effective amount of a compound of the present invention. In certain embodiments, the lipoamide dehydrogenase is a *Mycobacterium tuberculosis* lipoamide dehydrogenase. In other embodiments, the present invention relates to a method for inhibiting pyruvate dehydrogenase activity comprising contacting a pyruvate dehydrogenase with an effective amount of a compound of the present invention. In certain embodiments, these methods are in vivo methods, and the method comprises administering a compound of the present invention to a subject in need thereof, e.g., a subject infected with a pathogen dependent upon one or more of these enzymes for survival, e.g., *tubercle bacillus, Pseudomonas aeruginosa*, or *Trypanosoma brucei*. In certain embodiments, these methods are in vitro methods, e.g., assay methods performed on cells or tissue culture. Suitable in vitro assays can be used to preliminarily evaluate the efficacy of the above-described compounds in inhibiting Lpd and/or PDH activity. The compounds can then be further examined for their efficacy in treating the infection. For example, a compound of the present invention exhibiting Lpd and/or PDH inhibitory activity can be administered to an animal (e.g., a rabbit model) having an infection, e.g., an infection with *tubercle bacillus, Pseudomonas aeruginosa*, or *Trypanosoma brucei*, and its therapeutic effects assessed. Based on the results, an appropriate dosage range and administration route can also be determined Other methods contemplated by the present invention include treatment of a tuberculosis infection with an effective amount of an extract of Wu-Bei-Zi, also referred to as the Gallnut of Chinese Sumac, alone or in combination with a compound of the present invention, or pharmaceutical composition thereof, to a subject in need thereof. In certain embodiments, the effective amount of Wu-Bei-Zi is a therapeutically effective amount. In certain embodiments, the effective amount of Wu-Bei-Zi is a prophylactically effective amount.

EXAMPLES

In order that the invention described herein may be more fully understood, the following examples are set forth. It should be understood that these examples are for illustrative purposes only and are not to be construed as limiting this invention in any manner.

Biological Assays

Lipoamide Dehydrogenase (Lpd) Inhibition Assay

The assay was performed in a manner similar to that described in Bryk et al., *Biochemistry* (2010) 49:1616-1627 and modified for an online robotics screening system.

A solution containing Lpd (100 nM) and 100 mM sodium phosphate buffer (pH 7.0) was prepared. Another solution containing the substrate lipoamide (2 mM), 100 mM sodium phosphate buffer (pH 7.0), EDTA (4 mM), and NADH (200 µM) was also prepared. The detection reagent, DTNB was dissolved in DMSO and diluted to a concentration of 375 µM with a 100 mM sodium phosphate buffer (pH 7.0).

4 µL/well of Lpd solution was dispensed into 1536-well clear bottom plates. Next, 50 nL of each test compounds (1 mM dissolved in DMSO) was added into each well. After one hour of incubation, 4 µL/well of lipoamide (LPA) solution was added, so that in each well, the concentrations of Lpd, LPA, and the test compound were 50 nM, 1 mM, and 6.25 µM, respectively. The reaction was allowed to progress for 5 minutes, and then 2 µL/well of DTNB solution was added, which led to a DTNB concentration of 75 µM. The optical density of each well was then obtained at the wavelength of 405 nm (OD405 nm).

PDH Inhibition Activity

Mtb PDH (Lpd+DlaT+AceE) is provided by Dr. Bryk Ruslana. The assay was performed in a manner similar to that described in Bryk et al., *Biochemistry* (2010) 49:1616-1627 and modified for an online robotics screening system.

A solution containing PDH (Lpd=15 µM; DlaT=30 µM; AceE=15 µM) was diluted 2-fold in 100 mM of potassium phosphate buffer (pH 7.0) for the assay. Another reaction solution containing 50 mM potassium phosphate buffer (pH 7.0), 200 µM TPP, 2 mM Pyruvate, 200 µM CoA, 1 mM MgCl$_2$, 1 mM NAD+ was prepared. 5 µL/well of PDH solution was dispensed into 1536-well black plates. Next, 50 nL of each test compound (1 mM dissolved in DMSO) was added into each well. After 30 minutes of incubation, 5 µL/well of reaction solution was added. At the 30th minutes of the reaction, the florescence signal (excitation 360 nm and emission 460 nm) was obtained by Viewlux reader (PerkinElmer).

In Vitro Antitubercular H37Rv. Agar Dilution Assay: MIC Assay

*Mycobacterium tuberculosis* strains H37Rv were obtained from Centers for Disease Control (CDC) of Taiwan. Mtb H37Rv cells were cultured at 37° C. in Middlebrook 7H9 (containing 10% OADC, 0.2% glycerol).

The MIC test was performed in 96-well plates. Two-fold dilutions of each test compound were prepared in the 100 µL/well of 7H9 medium (containing 10% OADC). The final compound concentration was 8~0.25 µg/mL. One hundred µL of H37Rv cells (3×10$^7$ cfu/mL) was inoculated to each well and the plate was were sealed and cultured at 37° C. for 7 days. After incubation time, 40 µL of 0.2% resazurin was added to each well and signal was read after additional 2 days. MIC was defined as the lowest drug concentration that prevented resazurin color change from blue to pink Minimum Inhibitory Concentration required for inhibition of the growth of *Mycobacterium tuberculosis* strains H37Rv.

Compounds

Compounds were obtained from a number of chemical libraries and screened for activity.

A compound library with 2 million compounds (the GRC-2M library), which consists of diversified synthetic compounds, was used for primary screening against Lpd enzyme activity. A total of 11,458 compounds ("primary hits") with an activity signal 1.5 folds greater than that of the median were identified from the primary screening. After reconfirmation with Lpd assay, 719 compounds were selected for PDH validation assay. A total of 61 potent compounds (IC50<µM) were selected for the inhibition assay against *Mycobacterium tuberculosis* strains.

Table Legend:

LPD IC$_{50}$: the half maximal inhibitory concentration of each compound required for 50% inhibition of LPD activity PDH IC$_{50}$: the half maximal inhibitory concentration of each compound required for 50% inhibition of PDH activity MIC: Minimum Inhibitory Concentration required for inhibition of the growth of *Mycobacterium tuberculosis* strains H37Rv.

Compounds

The compounds depicted below and herein may be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. The compounds can also be synthesized in manners similar to those described, e.g., in Brubaker et al., *J. Med. Chem.* (1986) 29:1094-1099; Limaye, *Chem. Ber.* (1934) 67:12-14, and Geetanjali et al., *Indian J. Chem. Sect. B* (1983) 22:164-165 with necessary modifications as recognized by those skilled in the art. Further guidance in the synthesis of compounds of the present invention is provided below.

For example, Compounds of Formula (IX), Table 1, may be synthesized following the guidance provided in PCT Patent Application Publication No. WO/2003/001968; U.S. Pat. No. 5,709,737; U.S. Pat. No. 5,563,014; U.S. Pat. No. 5,514,505; and U.S. Pat. No. 4,061,836, each of which is incorporated herein by reference in its entirety.

Compounds of Formula (X), Table 2, may be synthesized following the guidance provided in PCT Patent Application Publication No. WO/2011/000481; PCT Patent Application Publication No. WO/2010/003533; PCT Patent Application Publication No. WO/2005/007141; and PCT Patent Application Publication No. WO/2001/079209, each of which is incorporated herein by reference in its entirety.

Compounds of Formula (XII), Table 3, may be synthesized following the guidance provided in PCT Patent Application Publication No. WO/2006/116764, incorporated herein by reference in its entirety.

Compounds of Formula (XIV), Table 4, may be synthesized following the guidance provided in Patent Application No. KR 2009-31640, incorporated herein by reference in its entirety.

Compounds of Formula (XV), Table 5, may be synthesized following the guidance provided in Russ. Patent No. RU 2263667, incorporated herein by reference in its entirety.

Compounds of Formula (I), Table 6, may be synthesized following the guidance provided in PCT Patent Application Publication No. WO/2010/072807; PCT Patent Application Publication No. WO/2010/014798; and PCT Patent Application Publication No. WO/2004/007498, each of which is incorporated herein by reference in its entirety.

Compounds of Formula (II), Table 7, may be synthesized following the guidance provided in PCT Patent Application Publication No. WO/2009/088990, incorporated herein by reference in its entirety.

Compounds of Formula (V), Table 8, may be synthesized following the guidance provided in PCT Patent Application Publication No. WO/2011/043254; incorporated herein by reference in its entirety.

Compounds of Formula (VI), Table 9, may be synthesized following the guidance provided in PCT Patent Application Publication No. WO/2010/135608; and PCT Patent Application Publication No. WO/2002/026707, each of which is incorporated herein by reference in its entirety.

Compounds of Formula (VIII), Table 11, may be synthesized following the guidance provided in PCT Patent Application Publication No. WO 2010079238, incorporated herein by reference in its entirety.

Compounds of Formula (XVI), Table 12, may be synthesized following the guidance provided in PCT Patent Application Publication No. WO/2010/131921, incorporated herein by reference in its entirety.

A compound thus synthesized can be further purified by flash column chromatography, high performance liquid chromatography, crystallization, or any other suitable methods.

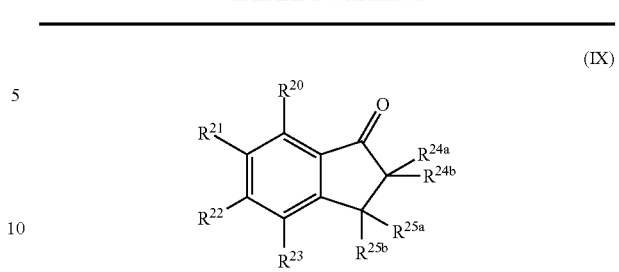

TABLE 3
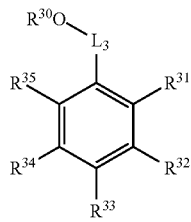
(XII)
| COMPOUND | | PDH IC$_{50}$ (μM) | MIC (μg/ml) |
|---|---|---|---|
| 301 |  | 0.76 | 8.0 |
| 302 | 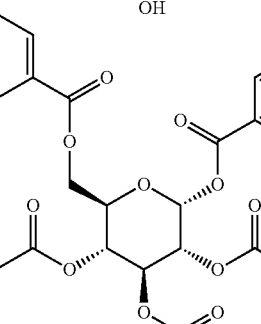 | 0.45 | >8.0 |
| 303 | 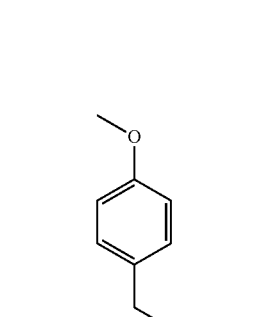 | <0.04 | 2.0 |

TABLE 4
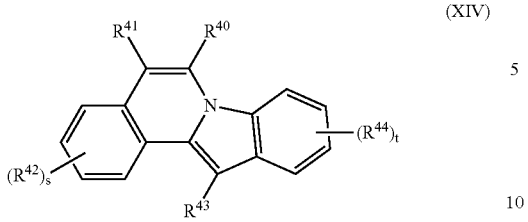
(XIV)
| COMPOUND | | PDH IC$_{50}$ (μM) | MIC (μg/ml) |
|---|---|---|---|
| 401 | 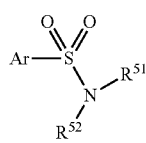 | 0.14 | >8.0 |
TABLE 5
(XV)
Ar—S(=O)(=O)—N(R$^{51}$)R$^{52}$
| COMPOUND | | LPD IC$_{50}$ (μM) | PDH IC$_{50}$ (μM) | MIC (μg/ml) |
|---|---|---|---|---|
| 500 | 5-bromo-2-amino-pyridine-3-sulfonyl-N-methyl-glycyl-(4-methoxyphenyl)amide | 0.96 ± 0.13 | 0.674 | >8.0 |
| 501 | N-(4-methylbenzyl)-1-((1-isopropyl-1H-imidazol-4-yl)sulfonyl)piperidine-4-carboxamide | 3.05 ± 1.05 | 3.126 | >8.0 |
| 502 | 5-bromo-2-amino-pyridine-3-sulfonyl-N-methyl-glycyl-(3,4-dimethoxyphenyl)amide | 0.84 ± 0.13 | — | — |

TABLE 5-continued
$$\text{Ar}-\overset{\overset{O}{\underset{\overset{\|}{S}}{\|}}}{\underset{\overset{|}{R^{52}}}{N}}-R^{51} \quad (XV)$$
| COMPOUND | LPD IC$_{50}$ (μM) | PDH IC$_{50}$ (μM) | MIC (μg/ml) |
|---|---|---|---|
| 503 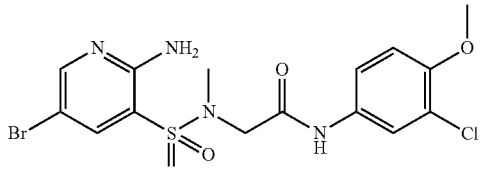 | 0.7 ± 0.08 | — | — |
| 504 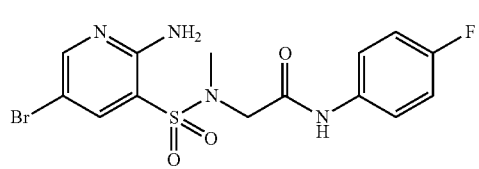 [SMILES: CN(CC(=O)Nc1ccc(F)cc1)S(=O)(=O)c1cc(Br)cnc1N] | 4.3 ± 1.21 | — | — |
| 505 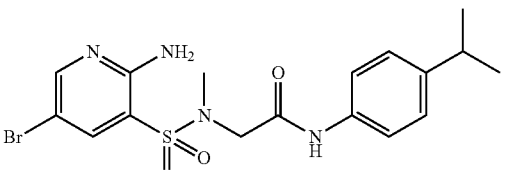 | 0.84 ± 0.11 | — | — |
| 506 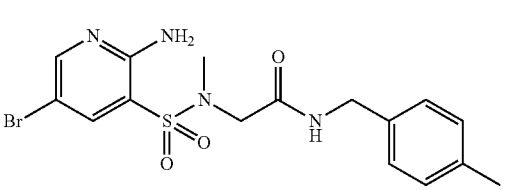 [SMILES: Cc1ccc(CNC(=O)CN(C)S(=O)(=O)c2cc(Br)cnc2N)cc1] | 3.31 ± 0.49 | — | — |
| 507 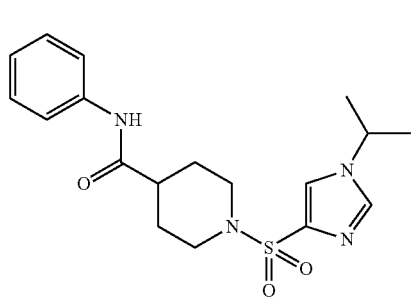 [SMILES: CC(C)n1cnc(S(=O)(=O)N2CCC(C(=O)Nc3ccccc3)CC2)c1] | 2.77 ± 0.69 | — | — |
| 508 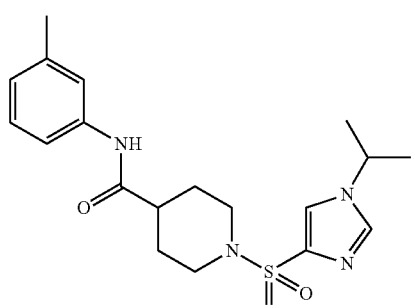 | 2.61 ± 0.82 | — | — |

TABLE 5-continued $$\text{Ar}-\overset{\overset{O}{\underset{\parallel}{S}}}{\underset{O}{\parallel}}-\overset{R^{51}}{\underset{R^{52}}{N}} \quad (XV)$$

| COMPOUND | LPD IC$_{50}$ (μM) | PDH IC$_{50}$ (μM) | MIC (μg/ml) |
|---|---|---|---|
| 509 | 2.87 ± 0.52 | — | — |
| 510 | 2.45 ± 0.21 | — | — |
| 511 | 2.55 ± 0.79 | — | — |
| 512 | 2.9 ± 0.71 | — | — |

TABLE 5-continued
(XV)
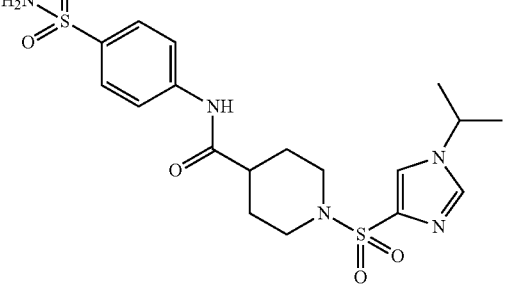
| COMPOUND | LPD IC$_{50}$ (μM) | PDH IC$_{50}$ (μM) | MIC (μg/ml) |
|---|---|---|---|
| 513 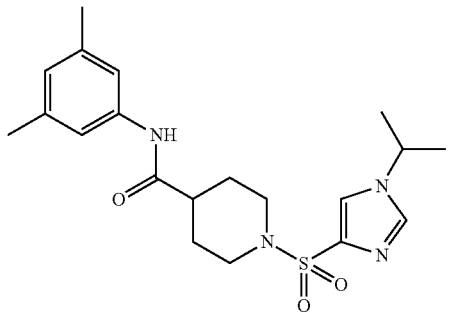 | 4.12 ± 1.81 | — | — |
| 514 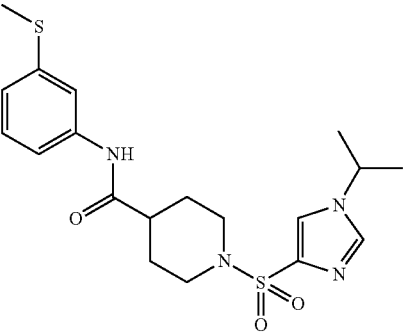 | 2.67 ± 0.57 | — | — |
| 515 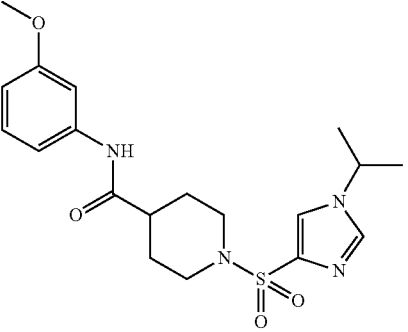 [SMILES: CCc1cccc(NC(=O)C2CCN(S(=O)(=O)c3cn(C(C)C)cn3)CC2)c1] | 4.81 ± 0.84 | — | — |
| 516 | 2.46 ± 0.76 | — | — |

TABLE 5-continued (XV)

| COMPOUND | LPD IC$_{50}$ (μM) | PDH IC$_{50}$ (μM) | MIC (μg/ml) |
|---|---|---|---|
| 517 (3-F phenyl) | 3.61 ± 0.98 | — | — |
| 518 (3-Cl phenyl) | 3.83 ± 0.78 | — | — |
| 519 (3-Br phenyl) | 2.76 ± 0.59 | — | — |
| 520 (4-ethoxy phenyl) | 2.17 ± 0.37 | — | — |

TABLE 5-continued (XV)

| COMPOUND | LPD IC$_{50}$ (μM) | PDH IC$_{50}$ (μM) | MIC (μg/ml) |
|---|---|---|---|
| 521 | 2.31 ± 0.36 | — | — |
| 522 | 2.94 ± 0.72 | — | — |
| 523 | 1.6 ± 0.48 | — | — |
| 524 | 2.67 ± 0.65 | — | — |

TABLE 5-continued $$\text{Ar}-\overset{\overset{\displaystyle O}{\|}}{\underset{\underset{\displaystyle O}{\|}}{S}}-\underset{R^{52}}{N}-R^{51} \quad (XV)$$

| COMPOUND | LPD IC$_{50}$ (µM) | PDH IC$_{50}$ (µM) | MIC (µg/ml) |
|---|---|---|---|
| 525 | 2.44 ± 0.58 | — | — |
| 526 | 2.79 ± 0.72 | — | — |
| 527 | 3.13 ± 0.79 | — | — |
| 528 | 1.83 ± 0.14 | — | — |

TABLE 5-continued (XV)

| COMPOUND | LPD IC$_{50}$ (μM) | PDH IC$_{50}$ (μM) | MIC (μg/ml) |
|---|---|---|---|
| 529 | 3.92 ± 2.47 | — | — |
| 530 | 2.07 ± 0.71 | — | — |
| 531 | 4.11 ± 1.59 | — | — |
| 532 | 2.85 ± 0.51 | — | — |

TABLE 5-continued $$\text{Ar} - \overset{O}{\underset{O}{S}} - \overset{R^{51}}{\underset{R^{52}}{N}} \quad (XV)$$

| COMPOUND | | LPD IC$_{50}$ (μM) | PDH IC$_{50}$ (μM) | MIC (μg/ml) |
|---|---|---|---|---|
| 533 | 3-Cl-4-methylphenyl-NH-C(O)-piperidine-N-SO$_2$-(1-isopropyl-imidazol-4-yl) | 2.64 ± 0.19 | — | — |
| 534 | 3-Cl-4-methoxyphenyl-NH-C(O)-piperidine-N-SO$_2$-(1-isopropyl-imidazol-4-yl) | 1.69 ± 0.38 | — | — |
| 535 | 3-(isoxazol-5-yl)phenyl-NH-C(O)-piperidine-N-SO$_2$-(1-isopropyl-imidazol-4-yl) | 2.12 ± 0.21 | — | — |
| 536 | benzyl-NH-C(O)-piperidine-N-SO$_2$-(1-isopropyl-imidazol-4-yl) | 2.69 ± 0.8 | — | — |

TABLE 5-continued $$\text{Ar}-\underset{\underset{O}{\overset{O}{\|}}}{\overset{\|}{S}}-\underset{R^{52}}{N}-R^{51} \quad \text{(XV)}$$

| COMPOUND | LPD IC$_{50}$ (μM) | PDH IC$_{50}$ (μM) | MIC (μg/ml) |
|---|---|---|---|
| 537 | 3.4 ± 1.6 | — | — |
| 538 | 2.54 ± 0.57 | — | — |
| 539 | 4.3 ± 1.66 | — | — |
| 540 | 4.18 ± 1.09 | — | — |

TABLE 5-continued (XV)

Ar—S(=O)(=O)—N(R51)(R52)

| COMPOUND | LPD IC$_{50}$ (μM) | PDH IC$_{50}$ (μM) | MIC (μg/ml) |
|---|---|---|---|
| 541 | 3.31 ± 1.22 | — | — |
| 542 | 5.06 ± 1.09 | — | — |
| 543 | 3.97 ± 1.13 | — | — |
| 544 | 4.55 ± 1.27 | — | — |

TABLE 5-continued $$\text{Ar}-\overset{\overset{\displaystyle O}{\|}}{\underset{\underset{\displaystyle O}{\|}}{S}}-\underset{R^{52}}{\overset{\displaystyle R^{51}}{N}} \quad (XV)$$

| COMPOUND | LPD IC$_{50}$ (μM) | PDH IC$_{50}$ (μM) | MIC (μg/ml) |
|---|---|---|---|
| 545 | 2.69 ± 0.56 | — | — |
| 546 | 2.85 ± 0.78 | — | — |
| 547 | 2.67 ± 0.6 | — | — |
| 548 | 2.35 ± 0.52 | — | — |

TABLE 5-continued
(XV)
Ar—S(=O)(=O)—N(R51)(R52)
| COMPOUND | LPD IC$_{50}$ (µM) | PDH IC$_{50}$ (µM) | MIC (µg/ml) |
|---|---|---|---|
| 549 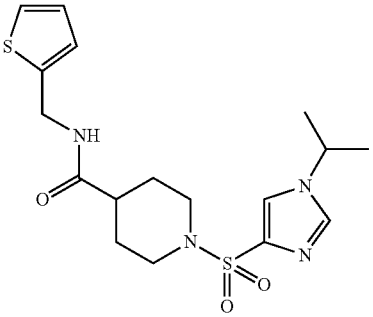 [SMILES: CC(C)n1cnc(S(=O)(=O)N2CCC(C(=O)NCc3cccs3)CC2)c1] | 3.42 ± 1.33 | — | — |
| 550 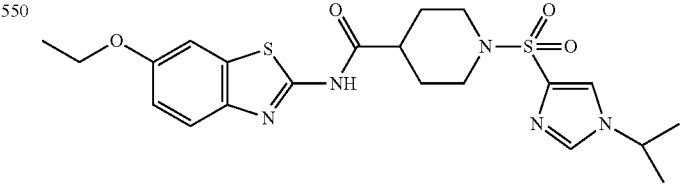 | 2.13 ± 0.24 | — | — |
| 551 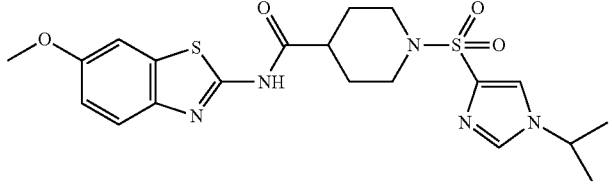 [SMILES: COc1ccc2nc(NC(=O)C3CCN(S(=O)(=O)c4cn(C(C)C)cn4)CC3)sc2c1] | 2.28 ± 0.11 | — | — |
| 552 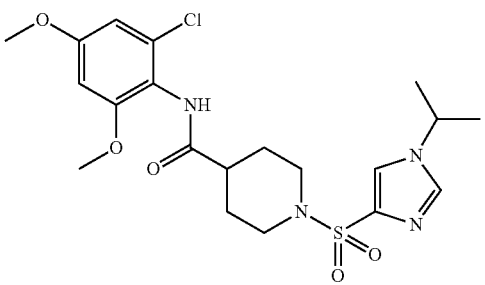 [SMILES: COc1cc(Cl)c(NC(=O)C2CCN(S(=O)(=O)c3cn(C(C)C)cn3)CC2)c(OC)c1] | 2.87 ± 0.67 | — | — |
| 553 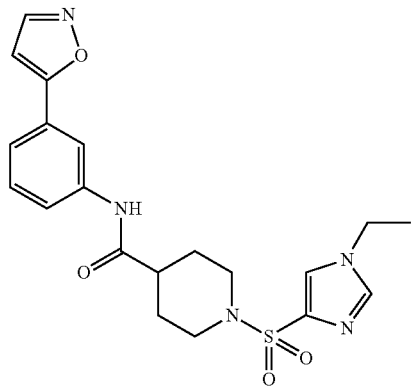 [SMILES: CCn1cnc(S(=O)(=O)N2CCC(C(=O)Nc3cccc(-c4ccno4)c3)CC2)c1] | 2.68 ± 0.99 | — | — |

TABLE 5-continued $$\text{Ar}-\underset{\underset{R^{52}}{|}}{\overset{\overset{O}{\|}}{\underset{\|}{S}}}-\underset{}{N}-R^{51} \quad \text{(XV)}$$

| COMPOUND | LPD IC$_{50}$ (μM) | PDH IC$_{50}$ (μM) | MIC (μg/ml) |
|---|---|---|---|
| 554 | 3.42 ± 0.88 | — | — |
| 555 | 3.2 ± 1.05 | — | — |
| 556 | 3.75 ± 1.01 | — | — |

TABLE 5-continued $$\text{Ar} - \underset{\underset{O}{\overset{O}{\|}}}{\overset{\|}{S}} - \underset{R^{52}}{\overset{R^{51}}{N}} \quad (XV)$$

| COMPOUND | LPD IC$_{50}$ (μM) | PDH IC$_{50}$ (μM) | MIC (μg/ml) |
|---|---|---|---|
| 557 | 3.55 ± 1.17 | — | — |
| 558 | 3.33 ± 0.8 | — | — |
| 559 | 2.99 ± 1.39 | — | — |

TABLE 5-continued $$\text{Ar}-\overset{\overset{\displaystyle O}{\|}}{\underset{\underset{\displaystyle R^{52}}{|}}{S}}-\underset{}{N}-R^{51} \quad\quad (XV)$$

| COMPOUND | LPD IC$_{50}$ (μM) | PDH IC$_{50}$ (μM) | MIC (μg/ml) |
|---|---|---|---|
| 560 | 3.86 ± 0.9 | — | — |
| 561 | 3.02 ± 1.78 | — | — |
| 562 | 3.5 ± 0.47 | — | — |
| 563 | 3.02 ± 0.87 | — | — |

TABLE 5-continued $$\text{Ar}-\underset{\underset{O}{\overset{O}{\|}}}{\overset{\|}{S}}-\underset{R^{52}}{\overset{R^{51}}{N}} \quad (XV)$$

| COMPOUND | LPD IC$_{50}$ (μM) | PDH IC$_{50}$ (μM) | MIC (μg/ml) |
|---|---|---|---|
| 564 | 2.22 ± 0.52 | — | — |
| 565 | 3.06 ± 0.47 | — | — |
| 566 | 3.91 ± 0.79 | — | — |

TABLE 6

(I)

| COMPOUND | LPD IC$_{50}$ (μM) | PDH IC$_{50}$ (μM) | MIC (μg/ml) |
|---|---|---|---|
| 601 | <0.04 | <0.04 | >8.0 |
| 602 | 0.23 ± 0.02 | <0.04 | >8.0 |
| 603 | 0.10 ± 0.01 | <0.04 | >8.0 |
| 604 | 0.14 ± 0.01 | <0.04 | >8.0 |
| 605 | 0.07 ± 0.01 | <0.04 | 8.0 |
| 606 | 0.96 ± 0.07 | 1.437 | >8.0 |

TABLE 6-continued

Structure (I): tricyclic core with R¹ on N (top), R² on N (bottom right), R³ on C (bottom left), with two C=O groups.

| COMPOUND | LPD IC$_{50}$ (μM) | PDH IC$_{50}$ (μM) | MIC (μg/ml) |
|---|---|---|---|
| 607 (R³ = 4-methoxyphenyl, R¹ = ethyl, R² = methyl) | 0.06 ± 0.01 | <0.04 | 8.0 |
| 608 (R³ = 3-pyridyl, R¹ = ethyl, R² = methyl) | 0.19 ± 0.03 | <0.04 | >8.0 |
| 609 (R³ = styryl, R¹ = ethyl, R² = methyl) | <0.04 | <0.04 | >8.0 |
| 610 (R³ = 2-thienyl, R¹ = ethyl, R² = methyl) | <0.04 | <0.04 | >8.0 |
| 611 (R³ = methyl, R¹ = methyl, R² = methyl) | 0.08 ± 0.01 | <0.04 | 4.0 |
| 612 (R³ = 3,4-methylenedioxyphenyl, R¹ = methyl, R² = methyl) | <0.04 | 0.439 | — |

TABLE 6-continued
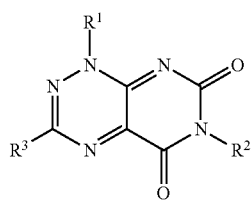
(I)
| COMPOUND | LPD IC$_{50}$ (μM) | PDH IC$_{50}$ (μM) | MIC (μg/ml) |
|---|---|---|---|
| 613 | <0.04 | <0.04 | — |
| 614 | <0.04 | <0.04 | — |
| 615 | <0.04 | <0.04 | — |
| 616 | <0.04 | <0.04 | — |
| 617 | <0.04 | <0.04 | — |

TABLE 6-continued (I)

| COMPOUND | LPD IC$_{50}$ (μM) | PDH IC$_{50}$ (μM) | MIC (μg/ml) |
|---|---|---|---|
| 618 | <0.04 | <0.04 | — |
| 619 | <0.04 | <0.04 | — |
| 620 | <0.04 | <0.04 | — |
| 621 | <0.04 | <0.04 | — |
| 622 | 2.16 ± 0.26 | — | — |

TABLE 7
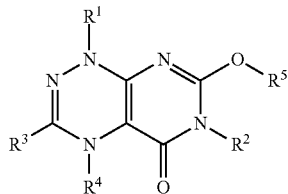
(II)
| COMPOUND | LPD IC$_{50}$ (μM) | PDH IC$_{50}$ (μM) | MIC (μg/ml) |
|---|---|---|---|
| 701 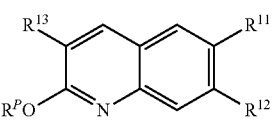 | — | <0.04 | >8.0 |
TABLE 8
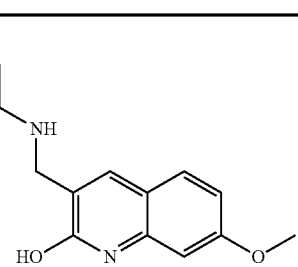
(V)
| COMPOUND | LPD IC$_{50}$ (μM) |
|---|---|
| 801 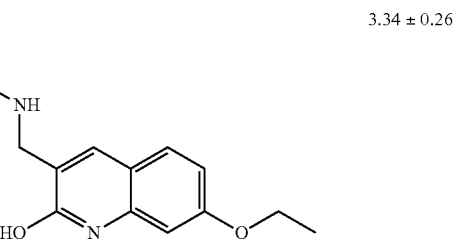 | 2.25 ± 0.16 |
| 802 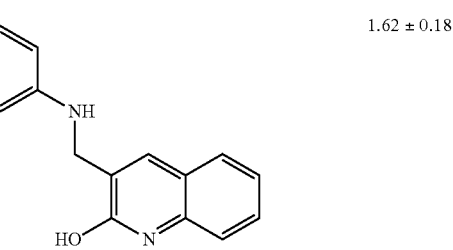 | 3.34 ± 0.26 |
| 803 | 1.62 ± 0.18 |

TABLE 8-continued
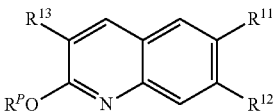
(V)
| COMPOUND | LPD IC$_{50}$ (μM) |
| --- | --- |
| 804 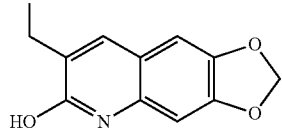 | 4.67 ± 0.57 |
| 805 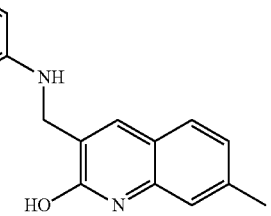 | 1.64 ± 0.14 |
| 806 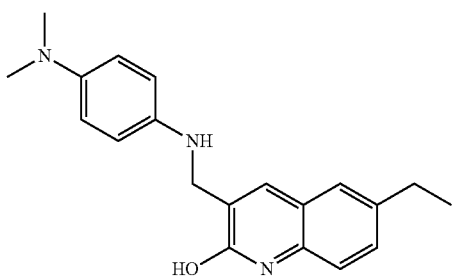 [SMILES: CCc1ccc2nc(O)c(CNc3ccc(N(C)C)cc3)cc2c1] | 4.73 ± 0.91 |
| 807 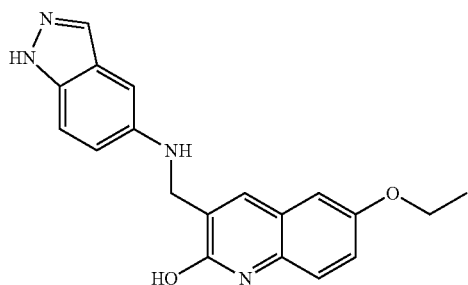 [SMILES: CCOc1ccc2nc(O)c(CNc3ccc4[nH]ncc4c3)cc2c1] | 4.54 ± 0.77 |

TABLE 9

(VI)

[Structure of formula VI: naphthoquinone with R11, R12 substituents and (R13)q]

| COMPOUND | LPD IC$_{50}$ (µM) | PDH IC$_{50}$ (µM) | MIC (µg/ml) |
|---|---|---|---|
| 901 (4-benzylamino-naphthalene-1,2-dione) | 0.1 ± 0 | 4.279 | 8.0 |
| 902 (2-amino-phenanthrene-9,10-dione) | 0.67 ± 0.07 | 0.788 | >8.0 |
| 903 (3,3-dimethyl pyrrole-fused naphthoquinone) | 0.86 ± 0.08 | 1.167 | >8.0 |
| 904 (2-nitro-phenanthrene-9,10-dione) | 0.64 ± 0.05 | 0.691 | >8.0 |
| 905 (2-phenyl-2H-naphtho[2,3-d][1,2,3]triazole-4,9-dione) | <0.04 | <0.04 | =8.0 |
| 906 (3-(1,2-dioxo-1,2-dihydronaphthalen-4-yl)pentane-2,4-dione) | 2.15 ± 0.43 | >5.0 | — |

TABLE 10
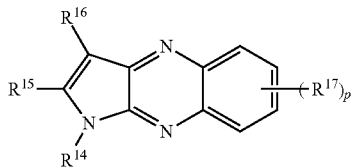
| COMPOUND | | LPD IC$_{50}$ (μM) | PDH IC$_{50}$ (μM) | MIC (μg/ml) |
|---|---|---|---|---|
| 1001 | | 1.08 ± 0.24 | 0.954 | >8.0 |
| 1002 | | 0.98 ± 0.15 | 3.315 | >8.0 |
| 1003 | | 0.52 ± 0.07 | >5.0 | — |
| 1004 | | 0.87 ± 0.1 | >5.0 | — |
| 1005 | | 0.9 ± 0.13 | >5.0 | — |

TABLE 10-continued
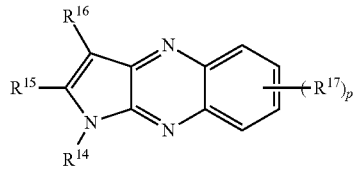
(VII)
| COMPOUND | LPD IC$_{50}$ (μM) | PDH IC$_{50}$ (μM) | MIC (μg/ml) |
|---|---|---|---|
| 1006 | 0.86 ± 0.16 | >5.0 | — |
| 1007 | 1.36 ± 0.16 | >5.0 | — |
| 1008 | 1.05 ± 0.14 | >5.0 | — |
| 1009 | 1.65 ± 0.23 | >5.0 | — |

TABLE 10-continued
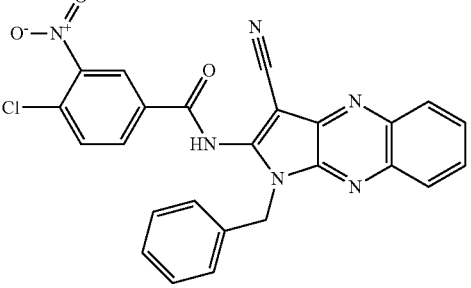
(VII)
| COMPOUND | LPD IC$_{50}$ (μM) | PDH IC$_{50}$ (μM) | MIC (μg/ml) |
|---|---|---|---|
| 1010 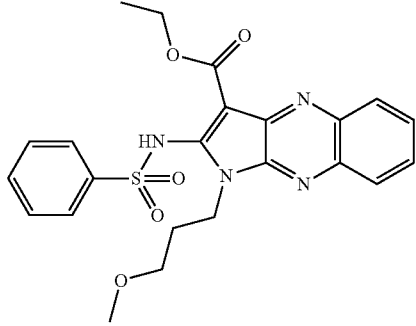 [SMILES: CCOC(=O)c1c(NS(=O)(=O)c2ccccc2)n(CCCOC)c2nc3ccccc3nc12] | >4.0 | >5.0 | — |
| 1011 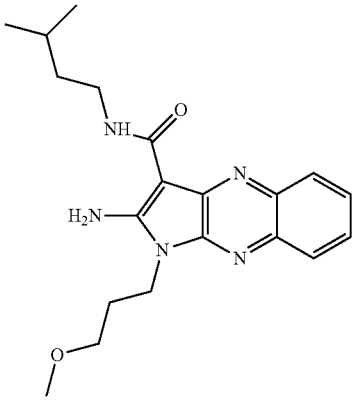 [SMILES: COCCCn1c(N)c(C(=O)NCCC(C)C)c2nc3ccccc3nc21] | 1.31 ± 0.16 | >5.0 | — |
| 1012 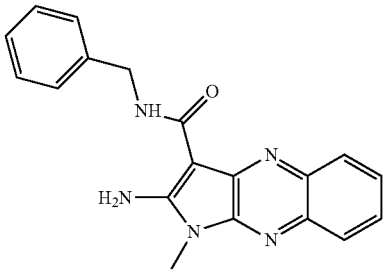 [SMILES: Cn1c(N)c(C(=O)NCc2ccccc2)c2nc3ccccc3nc21] | >4.0 | >5.0 | — |
| 1013 | >4.0 | >5.0 | — |

TABLE 11
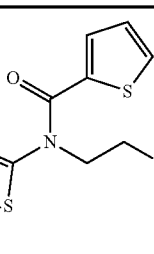
(VIII)
| COMPOUND | | LPD IC$_{50}$ (μM) |
|---|---|---|
| 1101 | 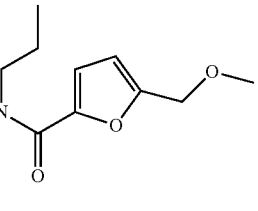 | 1.62 ± 0.24 |
| 1102 | 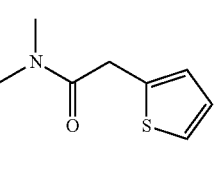 | 3.16 ± 0.43 |
| 1103 | 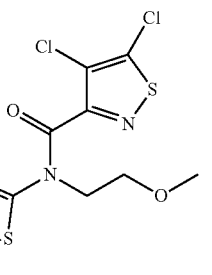 | 2.89 ± 0.46 |
| 1104 | 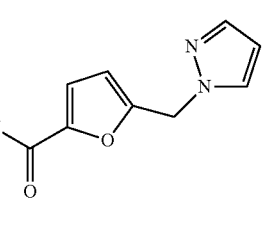 | 2.24 ± 0.26 |
| 1105 | 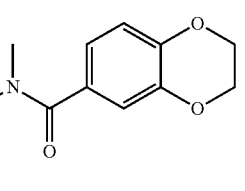 | 3.64 ± 0.51 |
| 1106 | | 2.67 ± 0.23 |

TABLE 11-continued (VIII)

| COMPOUND | | LPD IC$_{50}$ (μM) |
|---|---|---|
| 1107 | [structure] | 3.22 ± 0.5 |
| 1108 | [structure] | 3.76 ± 0.19 |

TABLE 12

(XVI)

| COMPOUND | LPD IC$_{50}$ (μM) | PDH IC$_{50}$ (μM) | MIC (μg/ml) |
|---|---|---|---|
| [structure: ethyl ester with Br] | 2.92 ± 0.88 | 1.653 | ≤0.25 |

OTHER EMBODIMENTS

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A method of treating a tuberculosis infection, the method comprising administering an effective amount of a compound of Formula (III) or (IV):

(III)

(IV)

or a pharmaceutically acceptable salt thereof, to a subject in need thereof;

wherein:

each of $R^6$, $R^7$, and $R^8$, independently, is H, optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, or optionally substituted heteroaryl;

each of $R^9$ and $R^{10}$, independently, is optionally substituted alkyl, optionally substituted alkenyl, optionally substituted alkynyl, optionally substituted cycloalkyl, optionally substituted cycloalkenyl, optionally substituted heterocycloalkyl, optionally substituted heterocycloalkenyl, optionally substituted aryl, optionally substituted heteroaryl, halo, nitro, —CN, —OR$_a$, —COOR$_a$, —OC(O)R$_a$, —C(O)R$_a$, —C(O)NR$_b$R$_c$, or —NR$_b$R$_c$;

each instance of R$_a$ is independently hydrogen, optionally substituted alkyl, optionally substituted cycloalkyl, optionally substituted cycloalkenyl, optionally substituted heterocycloalkyl, optionally substituted heterocycloalkenyl, optionally substituted aryl, or optionally substituted heteroaryl;

each instance of R$_b$ and R$_c$ is, independently, hydrogen, optionally substituted alkyl, optionally substituted cycloalkyl, optionally substituted cycloalkenyl, optionally substituted heterocycloalkyl, optionally substituted heterocycloalkenyl, optionally substituted aryl, optionally substituted heteroaryl, an amino protecting group, or R$_b$ and R$_c$, together with the nitrogen atom to which they are bonded are an optionally substituted heterocycloalkyl, an optionally substituted heterocycloalkenyl, or an optionally substituted heteroaryl;

m is 0, 1, or 2; and n is 0, 1, 2, 3, 4, 5, 6, 7, 8, or 9.

2. The method of claim 1, wherein R$^7$ is hydrogen, and R$^8$ is optionally substituted alkyl, optionally substituted cycloalkyl, optionally substituted heterocycloalkyl, optionally substituted aryl, or optionally substituted heteroaryl.

3. The method of claim 1, wherein R$^6$ is optionally substituted alkyl.

4. The method of claim 1, wherein each of m and n is 0.

5. The method of claim 1, wherein m is 1 and R$^9$ is halo.

6. The method of claim 1, wherein the compound is selected from the group consisting of:

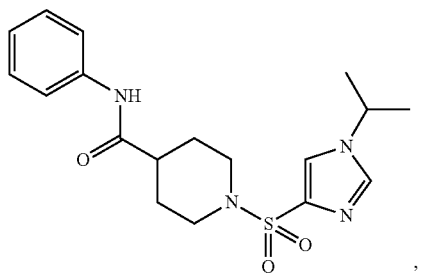

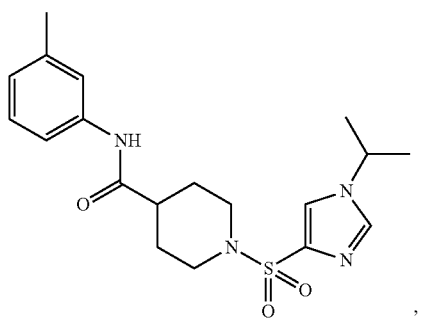

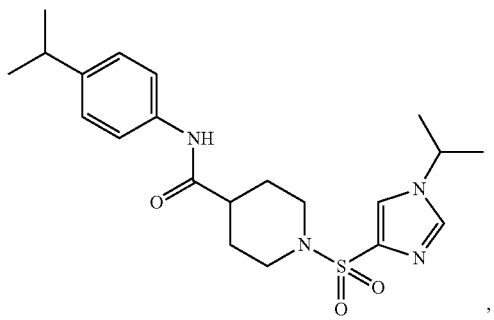

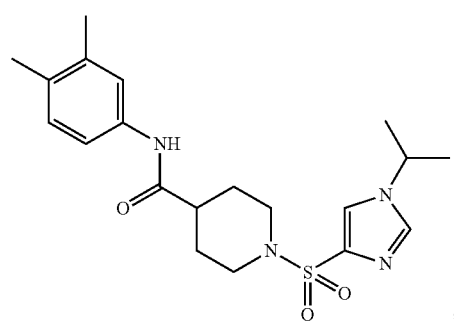

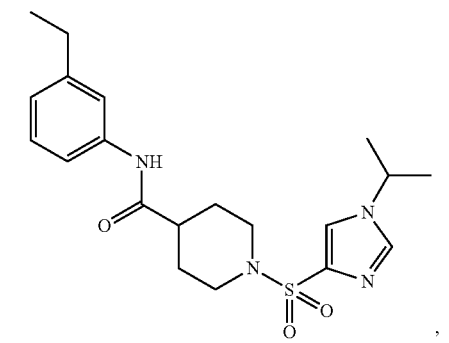

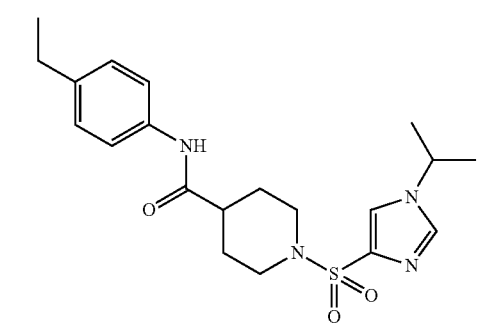

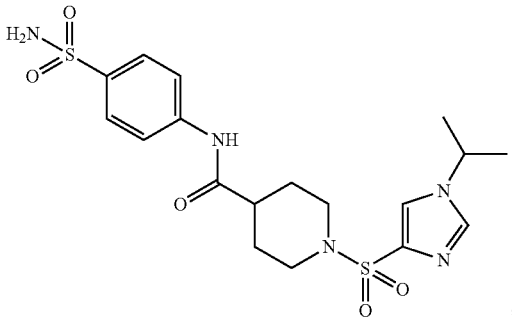

119
-continued
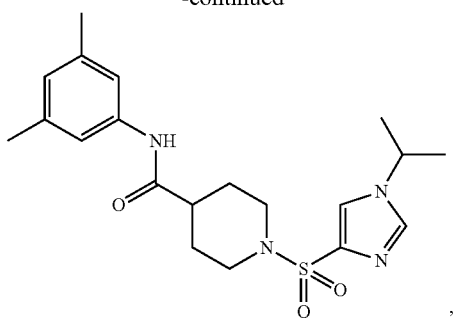
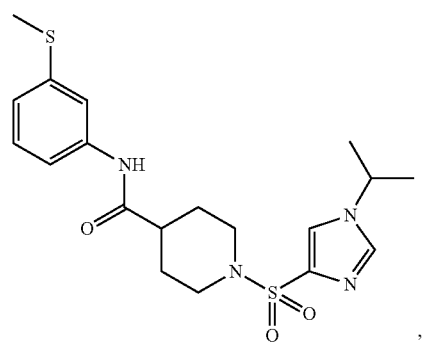
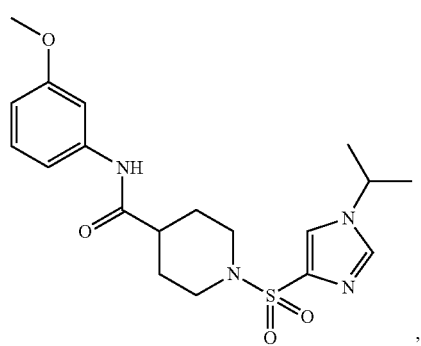
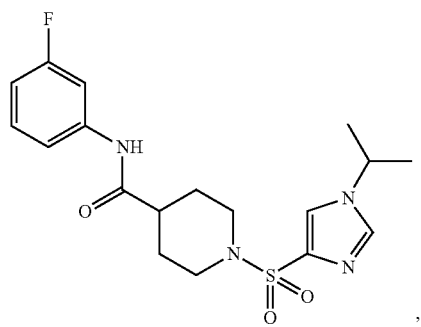
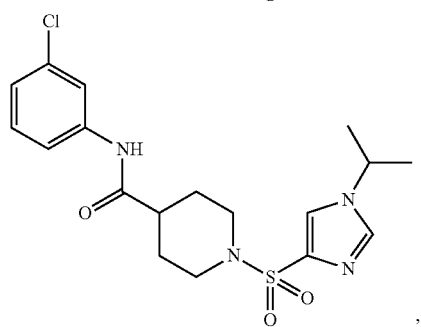
120
-continued
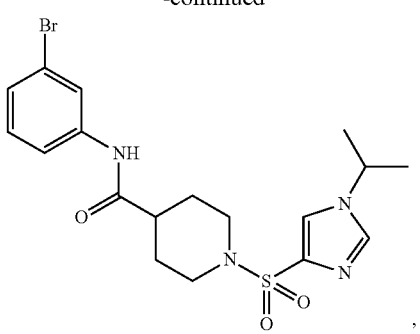
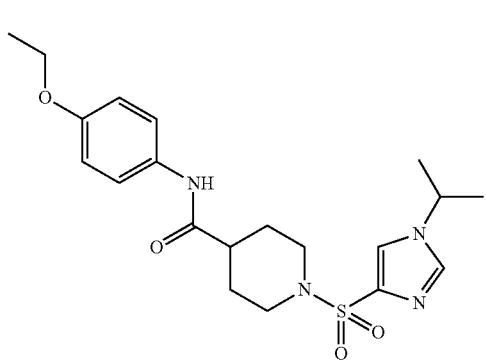
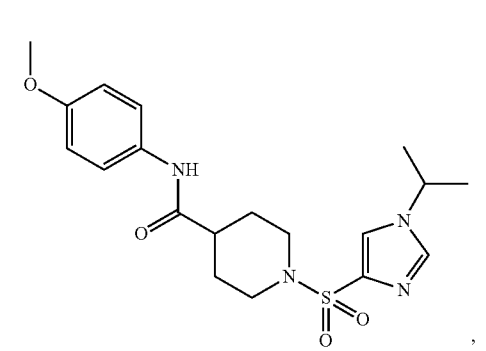
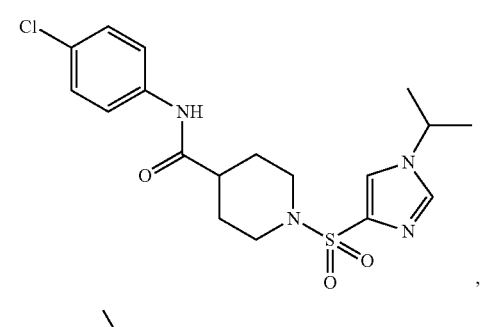
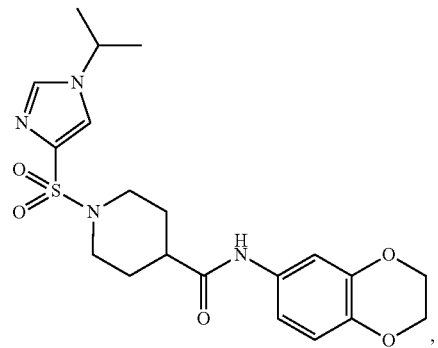

121
-continued
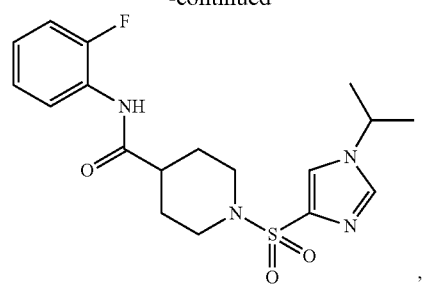
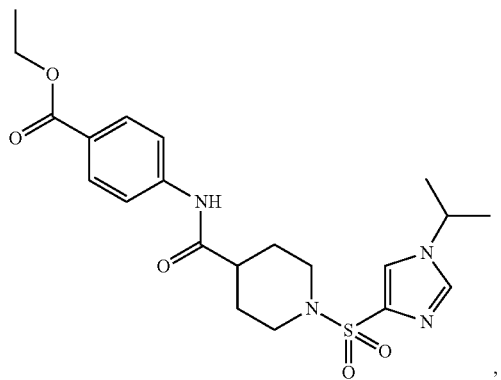
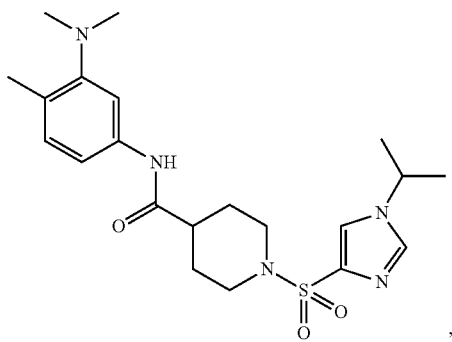
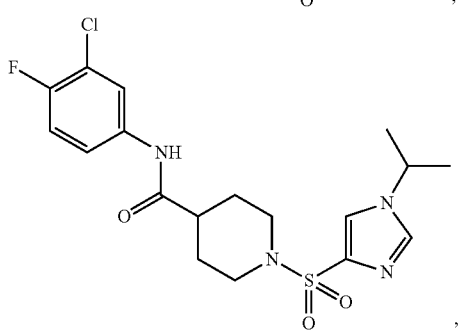
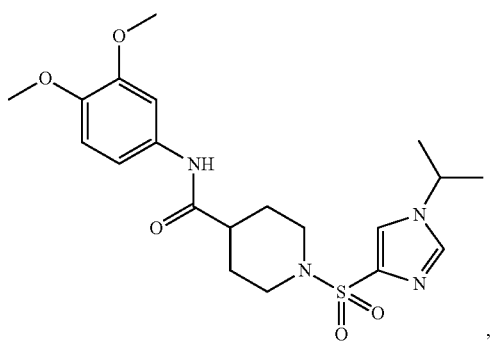
122
-continued
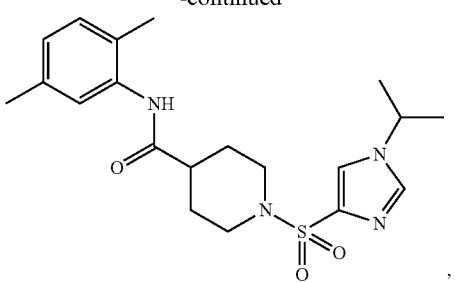
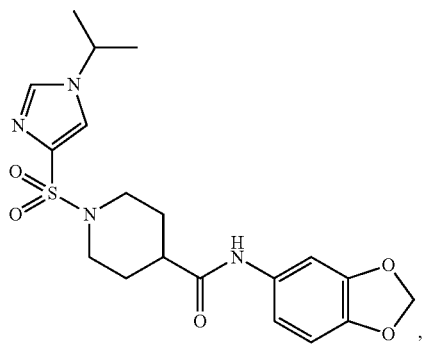
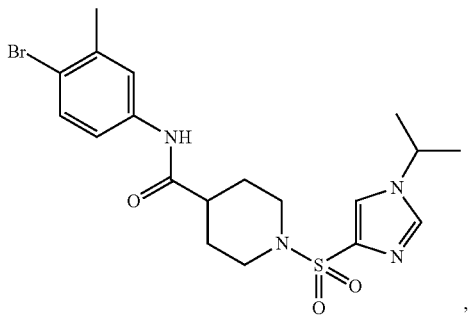
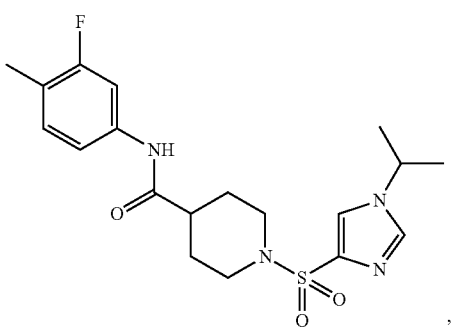
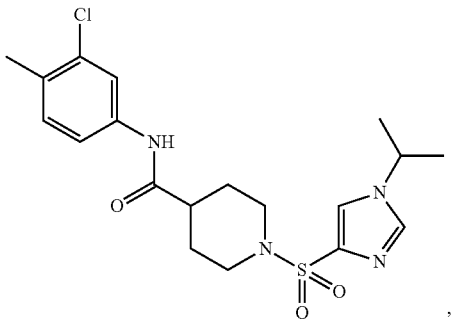

123
-continued
124
-continued
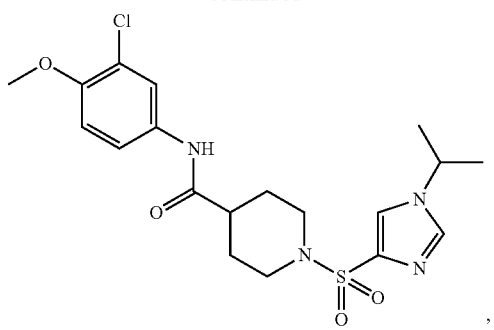
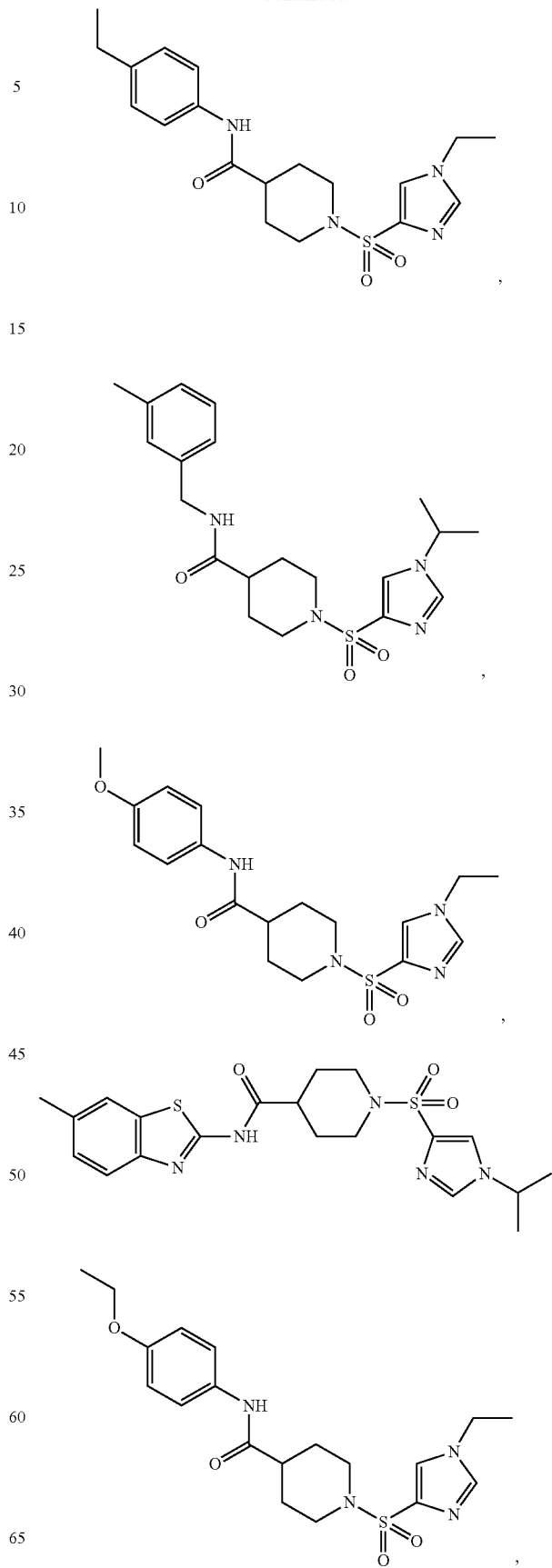

125
-continued
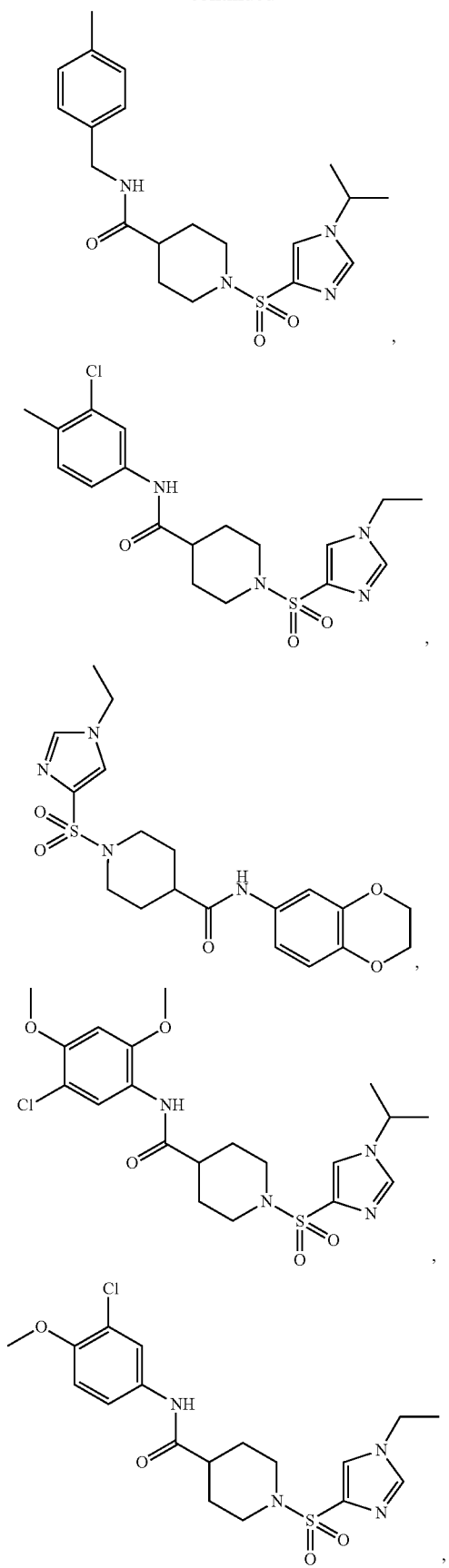
126
-continued
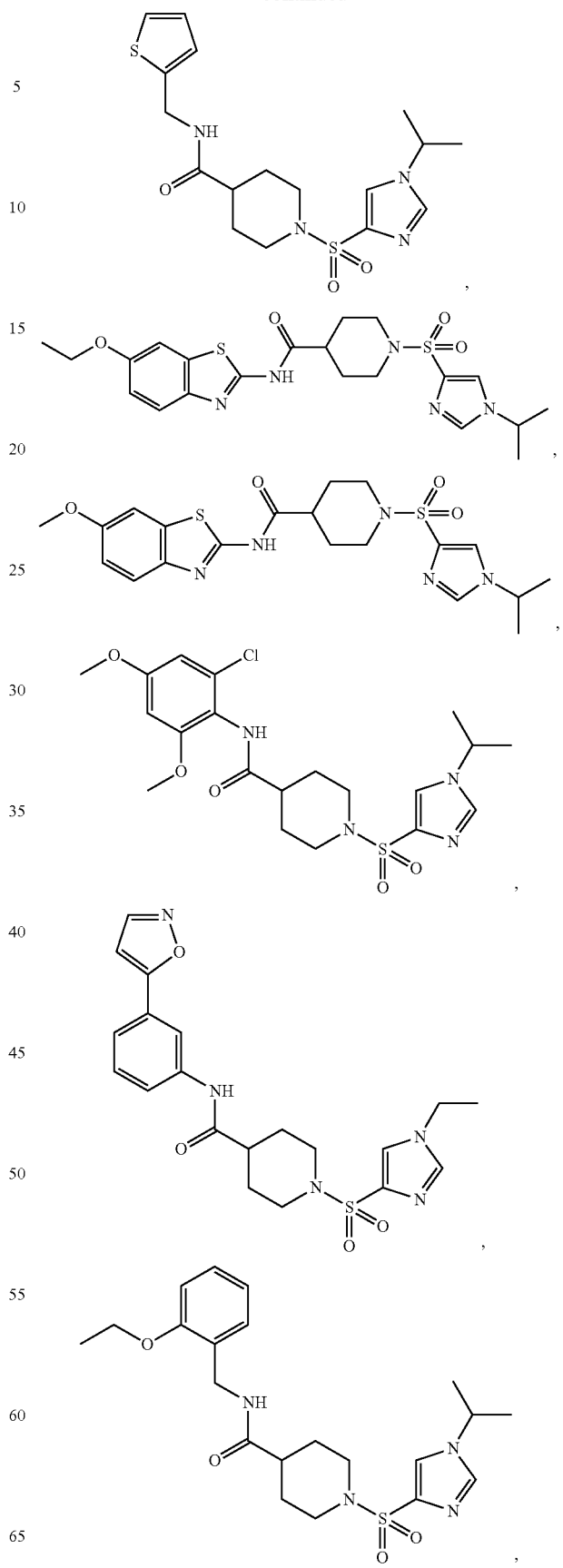

127
-continued
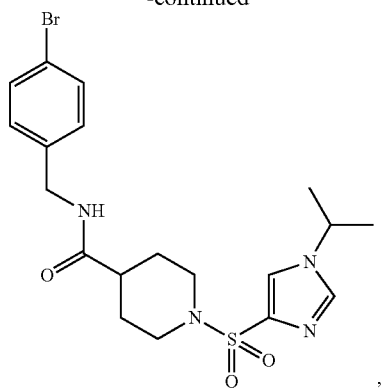
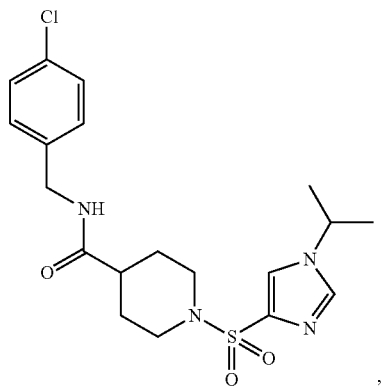
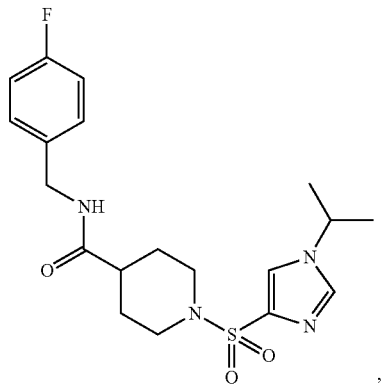
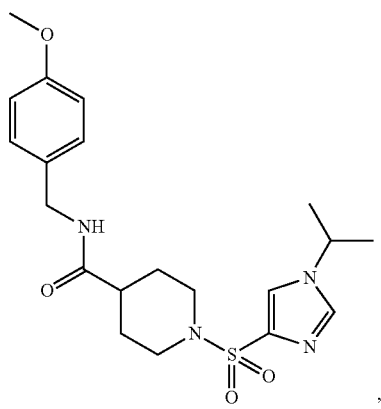
128
-continued
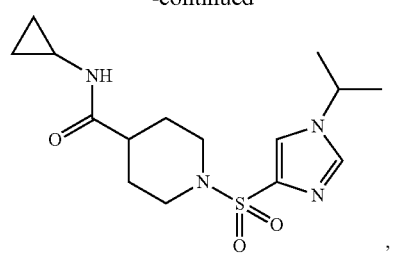
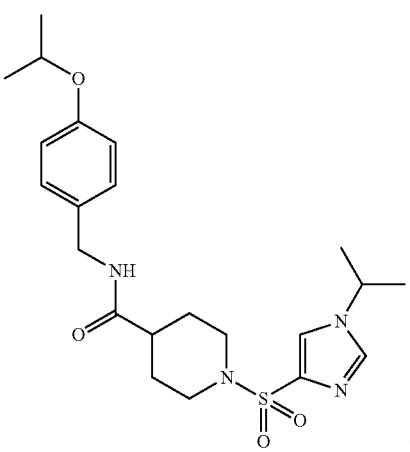
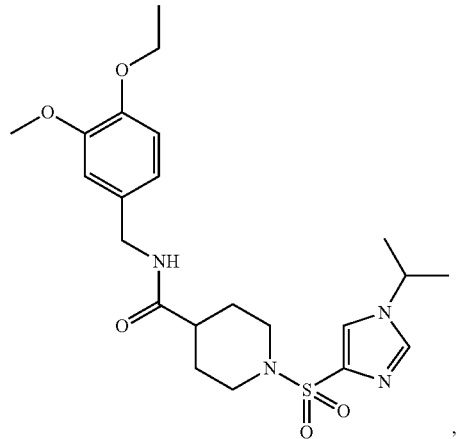
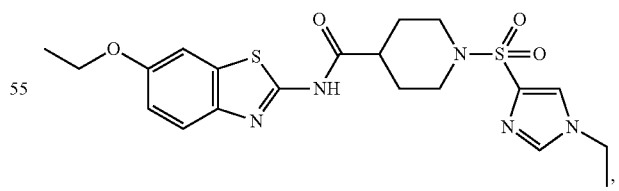
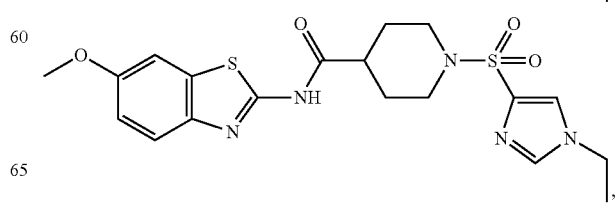

-continued

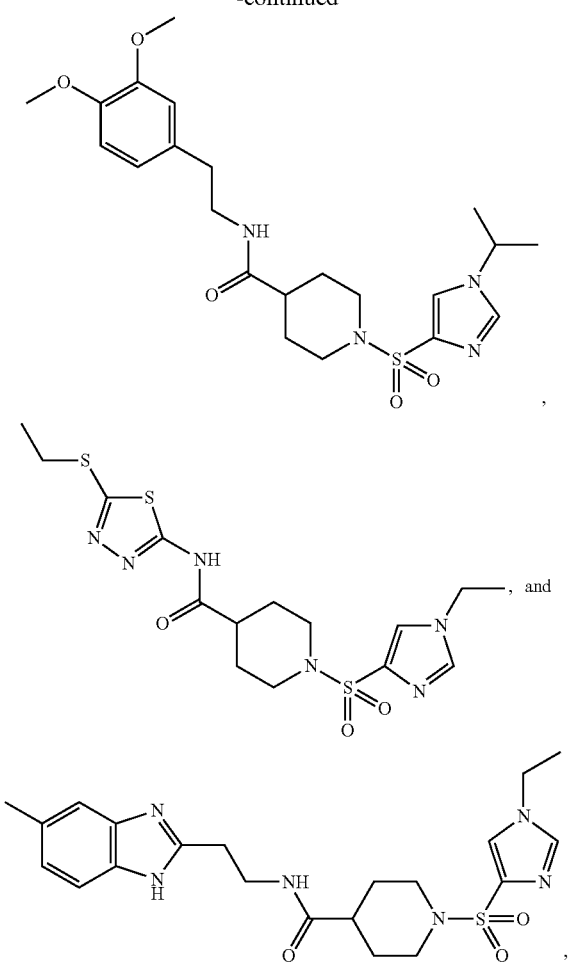

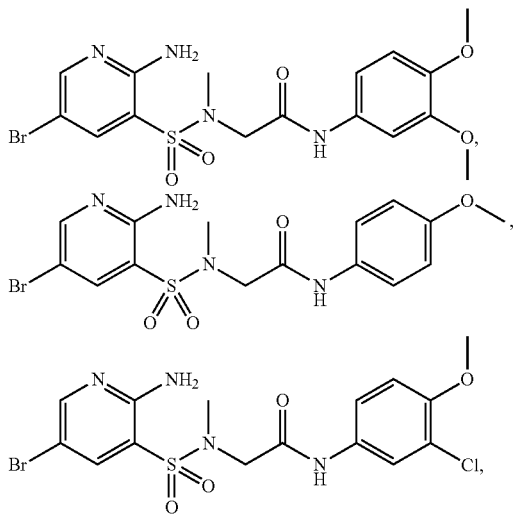

and pharmaceutically acceptable salts thereof.

7. The method of claim 1, wherein the compound is selected from the group consisting of:

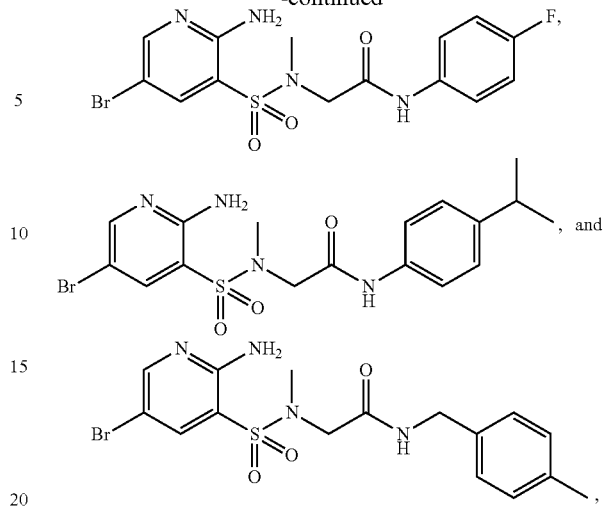

-continued

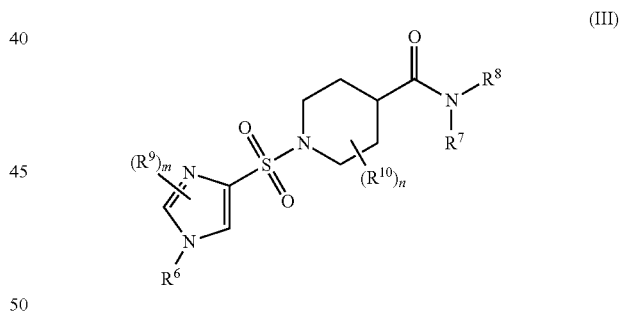

and pharmaceutically acceptable salts thereof.

8. The method of claim 3, wherein $R^6$ is unsubstituted alkyl.

9. The method of claim 7, wherein $R^6$ is —CH$_3$, —CH$_2$CH$_3$, or —CH(CH$_3$)$_2$.

10. The method of claim 2, wherein $R^8$ is optionally substituted aralkyl or heteroarylalkyl.

11. The method of claim 2, wherein $R^8$ is optionally substituted heteroaryl.

12. The method of claim 2, wherein $R^8$ is optionally substituted phenyl.

13. The method of claim 2, wherein $R^8$ is monosubstituted phenyl, disubstituted phenyl, or trisubstituted phenyl.

14. The method of claim 1, wherein the compound is of Formula (III)

(III)

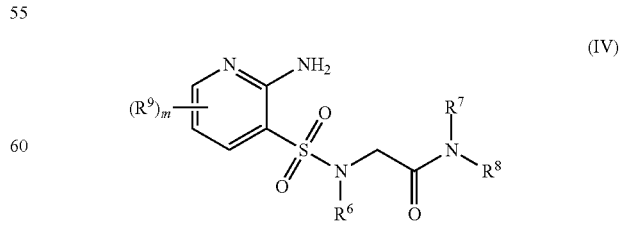

or a pharmaceutically acceptable salt thereof.

15. The method of claim 1, wherein the compound is of Formula (IV)

(IV)

or a pharmaceutically acceptable salt thereof.

16. The method of claim 1, wherein the effective amount is a therapeutically effective amount.

17. The method of claim 1, wherein the effective amount is a prophylactically effective amount.

18. The method of claim 1, wherein the tuberculosis infection is a *Mycobacterium tuberculosis* infection.

19. The method of claim 1, wherein the tuberculosis infection is a multi-drug-resistant tuberculosis (MDR-TB) infection.

20. The method of claim 1, wherein the tuberculosis infection is an extensively-drug-resistant tuberculosis (XDR-TB) infection.

* * * * *

UNITED STATES PATENT AND TRADEMARK OFFICE
CERTIFICATE OF CORRECTION

| | | |
|---|---|---|
| PATENT NO. | : 9,073,941 B2 | Page 1 of 1 |
| APPLICATION NO. | : 13/806228 | |
| DATED | : July 7, 2015 | |
| INVENTOR(S) | : Chi-Huey Wong et al. | |

It is certified that error appears in the above-identified patent and that said Letters Patent is hereby corrected as shown below:

In the Claims:

At column 130, line 25, claim 9, please change "The method of claim 7" to "The method of claim 8,"

At column 130, line 33, claim 13, please change "The method of claim 2" to "The method of claim 12,"

Signed and Sealed this
Twenty-ninth Day of December, 2015

Michelle K. Lee
*Director of the United States Patent and Trademark Office*